United States Patent
Ishihara et al.

(10) Patent No.: US 7,754,442 B2
(45) Date of Patent: Jul. 13, 2010

(54) REAGENT KIT FOR DETERMINING CHARACTERISTIC OF TISSUE

(75) Inventors: Hideki Ishihara, Miki (JP); Satoshi Nakayama, Kobe (JP); Yuko Kawasaki, Kobe (JP); Aya Katayama, Kakogawa (JP)

(73) Assignee: Sysmex Corporation, Kobe (JP)

( * ) Notice: Subject to any disclaimer, the term of this patent is extended or adjusted under 35 U.S.C. 154(b) by 702 days.

(21) Appl. No.: 11/529,998

(22) Filed: Sep. 29, 2006

(65) Prior Publication Data

US 2007/0077601 A1 Apr. 5, 2007

(30) Foreign Application Priority Data

Sep. 30, 2005 (JP) .............................. 2005-289460

(51) Int. Cl.
  *G01N 33/53* (2006.01)
(52) U.S. Cl. ........................ 435/7.4; 435/7.5; 435/7.91; 435/7.94; 435/810; 436/808; 422/61
(58) Field of Classification Search ................... 435/7.4
  See application file for complete search history.

(56) References Cited

U.S. PATENT DOCUMENTS 6,753,157 B2 * 6/2004 Goueli ........................ 435/7.4
2002/0164673 A1 11/2002 Ishihara et al.

2004/0214180 A1 10/2004 Kobayashi et al.

OTHER PUBLICATIONS

Sueoka et al., Cancer Reseach. 1999. 59:3838-3844.*
Promega Technical Bulletin.*
Weisenthal, L.M.; Nygren, P. "Current Status of Cell Culture Drug Resistance Testing (CCDRT)"; 2002.
European Search Report for Application No. 06020582 dated Nov. 6, 2006.
Ishihara, Hideki et al. "A new cancer diagnostic system based on a CDK profiling technology." *Biochimica et Biophysica Acta*, 2005, 174, pp. 226-233.
Desai, Dipty et al. "Effects of phosphorylation by CAK on cyclin binding by CDC2 and CDK2." *Molecular and Cellular Biology*, 1995, 15, No. 1, pp. 345-350.

* cited by examiner

*Primary Examiner*—Bao-Thuy L Nguyen
(74) *Attorney, Agent, or Firm*—Brinks Hofer Gilson & Lione

(57) ABSTRACT

A reagent kit that is used for determining a characteristic of tissue obtained from a patient is described. The reagent kit comprising expression measurement reagents for measuring expression level of cyclin-dependant kinase (CDK) and activity measurement reagents for measuring activity value of CDK. The expression measurement reagents comprise first reagents and second reagents, and the activity measurement reagents comprise third reagents and fourth reagents. In the reagent kit, a first reagent set of the first and third reagents is stored under a first storage condition relating to temperature, and a second reagent set of the second and fourth reagents is stored under a second storage condition relating to temperature.

12 Claims, 27 Drawing Sheets i)

Cold storage reagent set

Frozen storage reagent set ii)

Cold storage reagent set

Frozen storage reagent set iii)

Cold storage reagent set

Frozen storage reagent set iv)

Cold storage reagent set

Frozen storage reagent set

Room temperature storage reagent set

REAGENT KIT FOR DETERMINING CHARACTERISTIC OF TISSUE

This application claims priority under 35 U.S.C. §119 to Japanese Patent Application No. JP2005-289460 filed Sep. 30, 2005, the entire content of which is hereby incorporated by reference.

BACKGROUND OF THE INVENTION

1. Field of the Invention

The present invention relates to a reagent kit for determining a characteristic of a tissue based on expression level and activity value obtained by measuring a cyclin-dependant kinase in the tissue sampled from a patient.

2. Description of the Related Arts

As the cell-cycle regulating factor governing cell proliferation of organisms, cyclin-dependant kinase (hereinafter, abbreviated as CDK) that is a positive regulating factor is present. Upon being exposed to activation such as phosphorylation or the like, CDK binds to cyclin resulting in a complex of CDK and cyclin (hereinafter, abbreviated as active type CDK in some cases). CDK is thus activated. In this way, CDK exhibits activity at particular stage of cell cycle according to the type thereof. Further, it has been known that cyclin-dependant kinase inhibitor (hereinafter, abbreviated as CDK inhibitor) that is a negative regulating factor binds to CDK and/or cyclin-CDK complex thereby inhibiting activity value of CDK.

Data of the expression level and the activity value of cell-cycle regulating factors may be used as convenient indexes for determining a characteristic of a tissue sampled from a patient such as type and malignancy of disorders associated to controls of cell cycle. For example, it is known that although expression of CDK in cells is normally constant, its expression becomes high in cells where proliferation is induced by a growth factor. However, as mentioned above, mechanism of activation of CDK is complicated one in which CDK, cyclin and CDK inhibitor are closely related and therefore, mere data of expression level of CDK, cyclin and CDK inhibitor, or mere data of activity value of CDK are not enough to be used as the indexes for determination of a characteristic of a tissue.

As used herein, "Expression level" denotes a target protein amount (units corresponding to number of molecules) obtained by measurement using tissue solution prepared from the tissue. Expression level can be determined by the conventional known method for determining amount of target protein from a protein mixture. For example, expression level can be determined using ELISA, western blotting, the method disclosed by U.S. Patent Application Publication No. 2004-0214180 or the like. A target protein can be trapped by using a specific antibody. In trapping of CDK1, for example, all of CDK1 (including CDK1 alone, complex of CDK1 and cyclin and/or CDK inhibitor, complex of CDK1 and other compounds) existing in said tissue solution can be trapped by using an anti-CDK1 antibody.

Further, CDK activity value denotes kinase activity level showing how many substrates (e.g., histone H1 for activated CDK1 and activated CDK2, Rb (Retinoblastoma protein) for activated CDK4 and activated CDK6) can be phosphorylated while CDK is bound to a specific cyclin, and is expressed by U (unit). In other words, it is possible to determine the activity value of CDK1 or CDK2 by checking how much histone H1 are phosphorylated by activated CDK1 or CDK2. Further, it is possible to determine the activity value of CDK4 or CDK6 by checking how much Rb (Retinoblastoma protein) is phosphorylated by activated CDK4 or CDK6. The activity value of CDK can be determined by conventional enzyme activity measurement method that uses radioactive materials as a label. Specifically, a method using 32P-labeled adenosine5'-O-(3-triphosphate) ($\gamma$-[32P]-ATP) is mentioned. With this method, monophosphoric group derived from 32P-labeled ATP is taken into a substrate by CDK action, and amount of 32P taken into a substrate is detected by autoradiography or scintillation counter to determine the amount of substrate being phosphorylated, and activity value of CDK is calculated from the amount of the substrate. Besides, U.S. Patent Application Publication No. 2002-01647673 discloses a measuring method without using radioactive materials as the label. Specifically, with this method, adenosine5'-O-(3-thiotriphosphate) (ATP-$\gamma$S) and a substrate are reacted, labeling material is bound to sulfur atom of mono-thiophosphoric acid group being taken into the substrate to determine the amount of labeling. For example, when a fluorescent material is used as the labeling material, fluorescent amount is measured as the amount of labeling.

At present, determination of a characteristic of a tissue sampled from a patient plays an important role at clinical scenes in terms of diagnosis of malignancy of cancers (easily develops metastasis, liable to recurrence, poor prognosis). For example, diagnosis of cancers is performed using information made available from measurements of tumor marker, tissue diagnosis and cytological diagnosis by biopsy, TNM classification (T: Size of primary focus, N: Level of lymph node metastasis, M: Distant metastasis), measurements of DNA content using fluorescent display type cell sorter or the like. However, the following problems are involved in each of the methods:

Diagnosis sensitivity is low.

Diagnosis is difficult since final judgment is made based on observer's own experiences.

Accurate forecasting of prognosis is not available though pathological condition is grasped at diagnosis.

Skilled technology is required.

These problems are directly reflected on the difference of judgment by individuals and of judgment by medical institutions in the diagnosis of malignancy of cancers, thereby resulting in a factor for scattering of diagnosis of malignancy of cancers.

In a case where therapeutic strategy of cancer should be established, checking of sensitivity of cells in the tissue to drugs such as anticancer agents is so important as well as diagnosis of malignancy. For methods to be used on such an occasion, anticancer agent sensitivity test for tumor cells performed in vitro is available, and MTT (3-(4,5 dimethylthiazole-2-yl)-2,5-diphenyltetrazoliumbromide) assay and DISC (Differential Staining Cytotoxicity) method are known. However, positive prediction rate of either of these methods is less than 70% which is insufficient to be used as the index to know whether or not anticancer agent treatment should be initiated (Weisenthal, L. M. and Nygren, P. (2002) Current status of cell culture drug resistance testing (CCDRT), http://weisenthal.org/). As mentioned above, measurement of expression level of CDK in a tissue sampled from a patient is disclosed by U.S. Patent Application Publication No. 2004-0214180, and measurement of activity value of CDK is disclosed by U.S. Patent Application Publication No. 2002-0164673, a kit for determining a characteristic of a tissue based on the expression level and the activity value of CDK has not been developed yet. Each of measurements of expression level of CDK and activity value of CDK involves a number of reagents and reagents with different storage conditions are mixed, which indicates that handling of these reagents is significantly cumbersome.

SUMMARY OF THE INVENTION

The object of the present invention is to provide a reagent kit for performing determination of a characteristic of a tissue taken from a patient which allows easy handling of each of reagents.

A first aspect of the present invention relates to a reagent kit for determining a characteristic of tissue obtained from a patient comprising: expression measurement reagents for measuring expression level of cyclin-dependant kinase (CDK) in the tissue, the expression measurement reagents comprising first and second reagents; and activity measurement reagents for measuring activity value of CDK in the tissue, the activity measurement reagents comprising third and fourth reagents; wherein a first reagent set of the first and third reagents is stored under a first storage condition relating to temperature, a second reagent set of the second and fourth reagents is stored under a second storage condition relating to temperature, and the second storage condition is different from the first storage condition.

A second aspect of the present invention relates to a reagent kit for determining a characteristic of tissue obtained from a patient comprising: first expression measurement reagents for measuring expression level of a first cyclin-dependant kinase (CDK) in the tissue, the first expression measurement reagents comprising first and second reagents; second expression measurement reagents for measuring expression level of a second CDK in the tissue, the second expression measurement reagents comprising third and fourth reagents; first activity measurement reagents for measuring activity value of the first CDK in the tissue, the first activity measurement reagents comprising fifth and sixth reagents; and second activity measurement reagents for measuring activity value of the second CDK in the tissue, the second activity measurement reagents comprising seventh reagent; wherein a first reagent set of the first, third, fifth and seventh reagents is stored under a first storage condition relating to temperature, a second reagent set of the second, fourth and sixth reagents is stored under a second storage condition relating to temperature, and the second storage condition is different from the first storage condition.

A third aspect of the present invention relates to a reagent kit for determining a characteristic of tissue obtained from a patient comprising: a labeled CDK antibody, a carrier to which a CDK antibody is immobilized, a substrate for the CDK and adenosine 5'-triphosphate (ATP); wherein the reagent kit stored under cold storage condition.

A fourth aspect of the present invention relates to a reagent kit for determining a characteristic of tissue obtained from a patient comprising: a CDK of predetermine concentration and labeling material which can bind to a reaction product of adenosine 5'-triphosphate (ATP) and a substrate for the CDK by action of the CDK; wherein the reagent kit stored under frozen storage condition.

DESCRIPTION OF THE PREFERRED EMBODIMENTS

Figure 1:
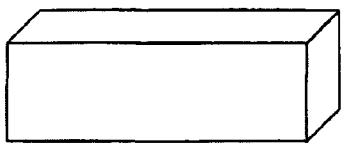
FIG. 1 is a drawing explaining a reagent kit of the embodiment according to the present invention.
Figure 1:
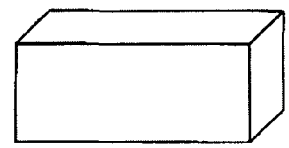
Figure 1:
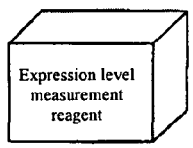
Figure 1:
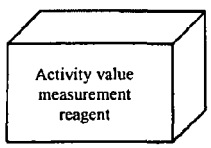
Figure 1:
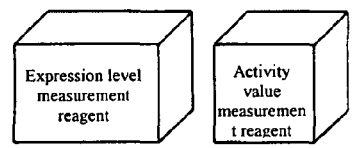
Figure 1:
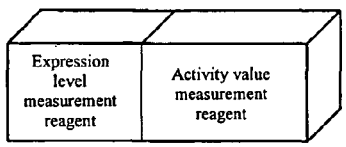
Figure 1:
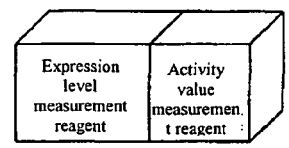
Figure 1:
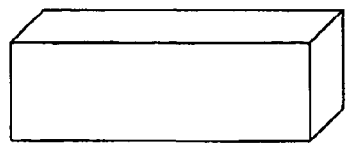
Figure 1:
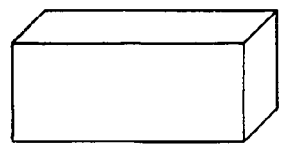
Figure 1:
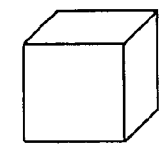

A reagent kit is designed to determine a characteristic of a tissue sampled from a patient and comprises expression measurement reagents used for measurement of expression level of cyclin-dependant kinase (CDK) in a tissue and activity measurement reagents used for measurement of activity value of CDK in a tissue. Of the expression measurement reagents and the activity measurement reagents, those being stored under a first storage condition relating to temperature constitute a first reagent set, and of the expression measurement reagents and the activity measurement reagents, those being stored under a second storage condition relating to temperature which are different from the first storage conditions constitute a second reagent set. With such a constitution, it is possible to store a number of reagents used for determination of a characteristic of a tissue sampled from a patient while being identified with ease by storage conditions thereof.

Here, the characteristic of a tissue sampled from a patient denote proliferation potency of cells contained in the tissue, sensitivity of cells contained in the tissue to drugs such as anticancer agent or the like, or malignancy of cancer of the tissue. Meanwhile, malignancy of cancer of the tissue means a level of occurrence risk of metastasis development, prone to cancer recurrence and poor prognosis. Prognosis of cancers and drug resistance test are made possible by determining the characteristic.

The following description explains embodiments of the reagent kit. However, it should be noted that the present invention is not limited to these embodiments.

The reagent kit of the embodiment comprises various reagents used for measurement of CDK expression level and various reagents used for measurement of CDK activity value.

(Group of Expression Level Measurement Reagents)

A group of expression level measurement reagents comprises labeled CDK antibody for CDK that is a measurement object. Labeled CDK antibody may be selected from antibodies against cyclin-dependant kinase selected from the group consisted of CDK1, CDK2, CDK4, CDK6, cyclin A dependant kinase, cyclin B dependant kinase, cyclin D dependant kinase and cyclin E dependant kinase. For materials for labeling CDK antibodies, fluorescent materials, enzymes or radioisotope may be used.

As for above-mentioned fluorescent materials, fluorescein, coumalin, eosin, phenanthroline, pyrene, rhodamine or the like are mentioned. Of these materials, fluorescein is preferably used. As for labeling enzymes, beta-galactosidase, alkaline phosphatase, peroxidases or the like are mentioned. Of them, peroxidases are preferably used. As for radioisotope, 32P is mentioned.

Further, the group of expression level measurement reagents preferably comprises CDK of predetermine concentration, protein of predetermine concentration being coded by housekeeping gene, labeled antibody for this protein, cyclin-dependant kinase inhibitor (CDK inhibitor) of predetermine concentration for said CDK, and antibody for the CDK inhibitor.

Besides, the group of expression level measurement reagents preferably comprises blocking solution for preventing chemical substances or the like other than labeled CDK antibodies from binding to CDK that bound to labeled CDK antibody.

Above-mentioned CDK of predetermine concentration, protein of predetermine concentration being coded by housekeeping gene, and CDK inhibitor of predetermine concentration are used for preparation of a calibration curve necessary to obtain each of expression level. For this reason, the group of expression level measurement reagents preferably comprises more than two types of reagents each having different concentration in such that it comprises CDK of a first concentration and CDK of a second concentration different from the first concentration.

Housekeeping gene is indispensable to existence of normal cells and may be selected from the group of genes expressing in almost all-cells. For example, GAPDH (glyceraldehyde-3-phosphate dehydrogenase) and beta-actin are mentioned.

CDK inhibitor can be selected appropriately by CDK as a measurement object. For example, when measurement object CDK is CDK1, p21 is mentioned; if CDK2, p21 or p27 mentioned; and if CDK4 and/or CDK6, p16 or p27 is mentioned.

For blocking solution, Block Ace (Block Ace powder is dissolved into purified water) (Dainippon Pharmaceutical Co., Ltd.), TBS-T (Tris Buffered Saline Tween), BSA (Bovine Serum Albumin) or the like may be used. For proteins, in addition to albumin, casein may be used.

Further, since the group of expression level measurement reagents performs background correction, it preferably comprises protein solution of predetermine concentration other than CDK. As an example of a protein of this sort, BSA is mentioned.

(Group of Activity Measurement Reagents)

A group of activity measurement reagents comprises a carrier in which CDK antibody is immobilized, a substrate that can be phosphorylated by, of CDK being trapped by this carrier, such one formed a complex with cyclin (active type CDK), adenosine5'-triphosphate (ATP) that is capable of reacting with this substrate and a labeling material capable of binding to a reaction product of ATP and the substrate by action of active type CDK.

The immobilized CDK antibody may be selected from antibodies for cyclin-dependant kinase selected from the group consisted of CDK1, CDK2, CDK4, CDK6, cyclin A-dependant kinase, cyclin B-dependant kinase, cyclin D-dependant kinase, and cyclin E-dependant kinase.

As carriers for immobilizing immobilized CDK antibodies, monolith silica gel, protein A sepharosebeads, protein G sepharosebeads or the like are mentioned.

Substrates which can be phosphorylated by, of CDK being trapped by CDK antibody immobilized to the carrier, active type CDK, can be selected appropriately by CDK of measurement object. Specifically, when CDK is CDK1 and/or CDK2, histone H1 is preferable, and when said CDK is CDK4 and/or CDK6, Rb (Retinoblastoma protein) is preferable.

Labeling materials and ATP can be selected appropriately. For example, when the labeling material is radioisotope, 32P-labeled adenosine5'-O-(3-triphosphate) (γ-[32P]-ATP) is mentioned. When the labeling material is fluorescent material or enzyme, adenosine5'-O-(3-thiotriphosphate) (ATP-γS) is mentioned.

Besides, the group of activity measurement reagents preferably comprises a column including a carrier in which CDK antibody is immobilized, a column including a carrier in which CDK antibody is not immobilized (blank column), buffer solution to allow appropriate reaction between CDK contained in a tissue solution prepared from a tissue sampled from a patient, and CDK antibody mobilized to the carrier, two types of column washing solutions for flushing away non-adsorptive materials not trapped by the carrier, a solution of predetermine concentration containing cytoplasm and intranuclear protein of mammalian cells, and a solution containing a protein for reduction of background.

Above-mentioned columns preferably comprise a portion for retaining the carrier and a portion for accumulating the solution. Further, the blank column may be used for background correction of results of measurements of activity.

For the buffer solution to allow appropriate reaction between the CDK antibody immobilized to the carrier and the CDK contained in the tissue solution, a solution containing surface active agent such as Nonidet-P40 and Tris-HCl pH7.4 may be used.

For two types of column washing solutions for flushing away non-adsorptive materials, 1) a solution containing surface active agent such as Nonidet-P40, Tris-HCl pH7.4, NaCl, 2) Tris-HCl pH7.4 or the like are used. It is preferable that after the CDK is trapped by the carrier, washing be made once by 1) and washing be made further once by 2).

The solution of predetermine concentration containing cytoplasm and intranuclear protein of mammalian cells preferably contains CDK of the measurement object. Besides, this CDK preferably comprises all amino acid sequences to be integrated originally as well as merely having a binding site with CDK antibody and is present while constructing three-dimensional structure (conformation) that is an original configuration.

For a solution containing proteins for reduction of the background, such one with similar composition as that of the blocking solution included in the group of expression level measurement reagents may be used. Specifically, 50% Block Ace (Block Ace powder is dissolved into purified water) (Dainippon Pharmaceutical Co., Ltd.), TBS-T (Tris Buffered Saline Tween), 4% BSA (Bovine Serum Albumin) or the like may be used. Besides, for proteins, casein may be used in addition to albumin.

The reagent kit preferably comprises, as reagents used commonly for the expression level measurement and the activity measurement, solubilization solution, measurement chips and washing solution. The solubilization solution is used for preparation of a tissue solution through solubilization of a tissue sampled from a patient. Measurement chips are equipped with a membrane that allows adsorption of proteins contained in a tissue solution and are used for measurements of the expression level and the activity value. A washing solution is used for washing of the membrane of measurement chips, or the like.

A solubilization solution is preferably a buffer solution containing surface-active agent, protease inhibitor and dephosphorylating enzyme inhibitor.

A surface-active agent is used to take-out intracellular substances by destroying cell membrane and nuclear membrane. However, those with such degree of surface activity that do not decompose active type CDK is used. For example, Nonidet-P40, Triton X-100, deoxycholic acid and CHAPS are mentioned. Concentration of the surface-active agent is preferably less than 1 w/v %.

The protease inhibitor is used, after cell membrane and nuclear membrane are destroyed, and intracellular substances are mixed, to prevent CDK and cyclin from being destroyed by degrading enzyme. For example, metallo-protease inhibitor such as EDTA and EGTA, serine protease inhibitor such as PMSF, trypsin inhibitor and chymotrypsin and/or mixture of cysteine protease inhibitor such as iodoacetamide and E-64, and such one available on the market in which is mixed protease inhibitor such as protease inhibitor cocktail (Sigma) in advance are mentioned.

The dephosphorylating ePzyme inhibitor is used to prevent phosphoric group of active type CDK per se from being hydrolyzed and to eventually prevent fluctuations of the activity. For example, sodium fluoride (NaF) is mentioned as serine/threonine dephosphorylating enzyme inhibitor, and ortho sodium vanadate (Na3VO4) is mentioned as tyrosine dephosphorylating enzyme inhibitor.

The measurement chip is preferably equipped with one or more wells. If provided one or more, when different samples are measured at once, the same sample may be measured by different concentrations.

For membrane at the bottom of the well, hydrophobic porous membrane is preferably used. For hydrophobic porous membrane, those capable of doing hydrophobic binding to proteins, specifically, PVDF (polyvinylidene-fluoride), hydrophobic membrane, nylon (charge prevented) membrane, cellulose nitrate or the like are mentioned. Pores of the hydrophobic porous membrane are 0.1 to 10 pim, preferably 0.1 to 0.5 μm. For hydrophobic porous membrane, those subjected to initial treatment such as permeation into methanol or the like are preferable.

Embodiments and storage conditions for each of reagents explained above are shown in Tables 1 to 6. Tables 1 to 3 show the group of expression level measurement reagents, Table 4 to 6 show the group of activity value measurement reagents, and Table 6 shows the reagent group used commonly for expression level measurements and activity value measurements. Unless otherwise specified, purified water is used as the solvent.

TABLE 1

Group of expression level measurement reagents

| Reagent No. | Reagent name | Ingredient | Final concentration | Total amount (ml) | State of preservation | Container name | Remarks |
|---|---|---|---|---|---|---|---|
| 1001 | Fluorescent labeling CDK1 antibody solution | Anti-CDK1 Fluorid-orange Block Ace | 4 μg/ml  80% | 0.3 | Cold | Screw cap | BlockAce: 4 g of Block Ace powder (UK-B80: Dainippon Pharmaceutical) is dissolved into 100 mL of purified water. |
| 1002 | Fluorescent labeling CDK2 antibody solution | Anti-CDK2 Fluorid-orange Block Ace | 4 μg/ml  80% | 0.3 | Cold | Screw cap | |
| 1003 | Fluorescent labeling p21 antibody solution | Anti-p21 Fluorid-orange Tris-HclpH7.4 NaCl BSA | 1 μg/ml  25 mM 150 mM 1% | 0.3 | Cold | Screw cap | Fluorid-orange: Supplied by IST |
| 1004 | Fluorescent labeling GAPDH antibody solution | Anti-GAPDH Fluorid-orange Tris-HclpH7.4 NaCl BSA | 8 μg/ml  25 mM 150 mM 1% | 0.3 | Cold | Screw cap | |

TABLE 1-continued

Group of expression level measurement reagents

| Reagent No. | Reagent name | Ingredient | Final concentration | Total amount (ml) | State of preservation | Container name | Remarks |
|---|---|---|---|---|---|---|---|
| 1005 | CDK1 antigen solution 1 | Recombinant CDK1<br>Nonidet-P40<br>Tris-HclpH7.4<br>NaCl | 0.01 µg/ml<br>0.005%<br>25 mM<br>150 mM | 0.1 | Frozen | Screw cap | |

TABLE 2

Group of expression level measurement reagents

| Reagent No. | Reagent name | Ingredient | Final concentration | Total amount (ml) | State of preservation | Container name | Remarks |
|---|---|---|---|---|---|---|---|
| 1006 | CDK1 antigen solution 2 | Recombinant CDK1<br>Nonidet-P40<br>Tris-HclpH7.4<br>NaCl | 0.1 µg/ml<br>0.005%<br>25 mM<br>150 mM | 0.1 | Frozen | Screw cap | |
| 1007 | CDK2 antigen solution 1 | Recombinant CDK2<br>Nonidet-P40<br>Tris-HclpH7.4<br>NaCl | 0.1 µg/ml<br>0.005%<br>25 mM<br>150 mM | 0.1 | Frozen | Screw cap | |
| 1008 | CDK2 antigen solution 2 | Recombinant CDK2<br>Nonidet-P40<br>Tris-HclpH7.4<br>NaCl | 0.1 µg/ml<br>0.005%<br>25 mM<br>150 mM | 0.1 | Frozen | Screw cap | |
| 1009 | P21 antigen solution 1 | Recombinant p21<br>Nonidet-P40<br>Tris-HclpH7.4<br>NaCl | 0.1 µg/ml<br>0.005%<br>25 mM<br>150 mM | 0.1 | Frozen | Screw cap | |
| 1010 | P21 antigen solution 2 | Recombinant p21<br>Nonidet-P40<br>Tris-HclpH7.4<br>NaCl | 0.1 µg/ml<br>0.005%<br>25 mM<br>150 mM | 0.1 | Frozen | Screw cap | |

TABLE 3

Group of expression level measurement reagents

| Reagent No. | Reagent name | Ingredient | Final concentration | Total amount (ml) | State of preservation | Container name | Remarks |
|---|---|---|---|---|---|---|---|
| 1011 | GAPDH antigen solution 1 | GAPDH<br>Nonidet-P40<br>Tris-HclpH7.4<br>NaCl | 0.01 µg/ml<br>0.005%<br>25 mM<br>150 mM | 0.1 | Frozen | Screw cap | GAPDH: SIGMA G6019 |
| 1012 | GAPDH antigen solution 2 | GAPDH<br>Nonidet-P40<br>Tris-HclpH7.4<br>NaCl | 0.1 µg/ml<br>0.005%<br>25 mM<br>150 mM | 0.1 | Frozen | Screw cap | |
| 1013 | Background solution | TBS<br>Nonidet-P40<br>BSA | 50 µg/ml<br>0.005%<br>4% | 0.1 | Cold | Screw cap | |
| 1014 | Blocking solution | Tris-HclpH7.4<br>NaCl<br>BSA | 25 mM<br>50 mM<br>4% | 5.0 | Cold | Twin simultaneous accessible container | |

TABLE 4

Group of activity measurement reagents

Figure 10:
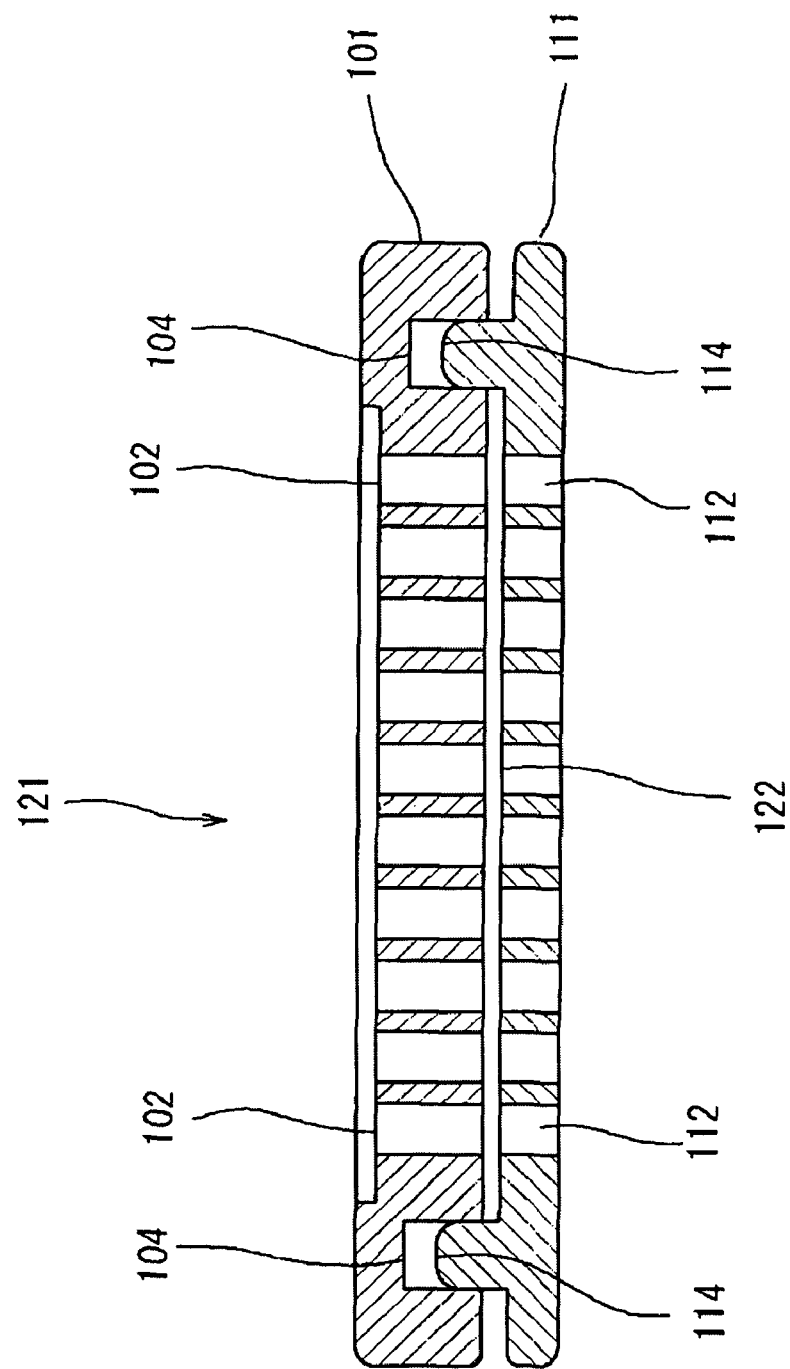
FIG. 10 is assembly sectional view of upper template shown in FIG. 6 and lower template shown in FIG. 6.

| Reagent No. | Reagent name | Ingredient | Final concentration | Total amount (ml) | State of preservation | Container name | Remarks |
|---|---|---|---|---|---|---|---|
| 2001 | CDK1 column | Anti-CDCK1 Monolith silica gel column | 4 μg/tube | | Cold | | Column having profile shown in FIG. 10 is used. 20% ethanol is included as preservative solution. |
| 2002 | CDK2 column | Anti-CDK1 Monolith silica gel column | 4 μg/tube | | Cold | | |
| 2003 | Blank column | Monolith silica gel column | | | Cold | | |
| 2004 | Immunoprecipitation buffer | Nonidet-P40<br>Tris-HclpH7.4 | 0.1%<br>50 mM | 0.1 | Cold | 2 ml Eppendorf tube | |
| 2005 | Before reaction buffer 1 | Nonidet-P40<br>Tris-HclpH7.4<br>Nacl | 0.1%<br>50 mM<br>300 mM | 2.0 | Cold | Twin simultaneous accessible container | |
| 2006 | Before reaction buffer 2 | Tris-HclpH7.4 | 50 mM | 2.0 | Cold | Twin simultaneous accessible container | |
| 2007 | Substrate solution | Tris-HclpH7.4<br>TritonX-100<br>MgCl$_2$<br>ATP-γS•4Li<br>Histone H1 | 40 mM<br>0.1%<br>20 mM<br>2 mM<br>10 μg | 1.0 | Cold | 2 ml Eppendorf tube | |

TABLE 5

Group of activity measurement reagents

| Reagent No. | Reagent name | Ingredient | Final concentration | Total amount (ml) | State of preservation | Container name | Remarks |
|---|---|---|---|---|---|---|---|
| 2008 | Fluorescence-labeling solution | 5-Iodoacetamide fluorescein (5-IAF)<br>Tris-HclpH7.4<br>EDTA-2Na<br>dimethyl sulfoxide (DMSO) | 1.2 mM<br>150 mM<br>5 mM | 0.4 | Frozen | Screw cap | DMSO is used as solvent |
| 2009 | Fluorescence enhancement reagent | Tris-HclpH7.4<br>NaCl 150 mM<br>BSA 4% | 25 mM<br>150 mM<br>4% | 2.0 | Cold | Twin simultaneous accessible container | |
| 2010 | Reaction stopper | 2-mercaptoethanol (ME)<br>Tris-HclpH7.4<br>NaCl 150 mM | 5%<br>25 mM<br>150 mM | 1.7 | Cold | 2 ml Eppendorf tube | |
| 2011 | Activity calibrator | K562 solubilization solution buffer | 1 μg/ul | 0.2 | Frozen | Screw cap | |

TABLE 6

Group of reagents commonly used for expression level and activity

| Reagent No. | Reagent name | Ingredient | Final concentration | Total amount (ml) | State of preservation | Container name | Remarks |
|---|---|---|---|---|---|---|---|
| 3001 | Tissue solubilization solution | Nonidet-P40<br>Tris-HclpH7.4<br>Ethylenediaminetetra acetic acid (EDTA)-2Na<br>sodium fluoride (NaF)<br>sodium orthovanadate (Na$_3$VO$_4$)<br>Protease-Inhibitor | 0.1%<br>50 mM<br>5 mM<br>50 mM<br>1 mM<br>0.2% | 0.4 | Frozen | 18 mL test tube | Protease-Inhibitor: SIGMA Protease-Inhibitor cocktail |

TABLE 6-continued

Group of reagents commonly used for expression level and activity

| Reagent No. | Reagent name | Ingredient | Final concentration | Total amount (ml) | State of preservation | Container name | Remarks |
|---|---|---|---|---|---|---|---|
| 3002 | Washing solution | Tris-HclpH7.4 NaCl | 25 mM 150 mM | 25 | Room temperature | 20 L Cubitainer | |
| 3003 | Measurement chip (Hydrophobic porous membrane) | Immobilon-FL | | | Room temperature | | Immobilon-FL: Milllipore |

To allow measurements of the expression level and the activity value of CDK contained in tissues, the present reagent kit contains the group of activity measurement reagents and the group of expression level measurement reagents as mentioned above. Particularly for solutions containing proteins such as antigen or the like, in order to prevent denaturation of proteins, handing should be made paying attention to storage conditions relating to temperature. From this, storage should be made under storage conditions suited for materials contained in each of reagents. Therefore, if reagents with same storage conditions are put into one set, storage under correct storage conditions is made easy, thereby ensuring that the present reagent kit is used under stable state. Storage conditions of each reagent are as shown in Tables 1 to 6.

FIG. 1 shows examples of package reagent groups. In illustration i), packages of reagents contained in the present reagent kit are divided according to storage conditions relating to temperature (cold storage, frozen storage). In ii), packages of reagents being divided according to storage conditions are further divided into a group of expression level measurement reagents and a group of activity value measurement reagents. In iii), reagents with same storage conditions are accommodated in the same package, and a space for a group of expression level measurement reagents and a space for a group of activity measurement reagents are provided in the package. By separating the group of expression level measurement reagents and the group of activity measurement reagents as illustrated in ii) and iii), when installing a reagent into a tissue characteristic determination apparatus, incorrect installation can be also prevented. For cases ii) and iii), a tissue solubilization solution (Reagent No. 3001), that is a reagent used commonly for the expression level measurement and the activity measurement, may be accommodated into either package or space of the cold storage reagent group. For a washing solution (Reagent No. 3002) and a measurement chip (Reagent No. 3003) which are stored under an room temperature, it is preferable to accommodate them into separate packages as illustrated in iv)

The preferable temperature of cold storage ranges between 2 and 10 degrees Celsius. The preferable temperature of frozen storage is less than zero degrees Celsius, and more preferable condition is less than −20 degrees Celsius. The preferable room temperature is less than 30 degrees Celsius.

Although the present reagent kit can be used for measurements by manual handling, the kit is preferably installed on an apparatus in which all processes are automated.

As an example of such apparatus, a tissue characteristic determination apparatus may be mentioned. The apparatus comprises a first data acquisition means for acquiring a first data reflecting expression level of CDK in a tissue sampled from a patient;

a second data acquisition means for acquiring a second data reflecting activity value of CDK in a tissue sampled from a patient;

an analytical means for acquiring, based on the first data and second data, information relating to a characteristic of the tissue.

With present reagent kit, after expression level and activity of two or more kinds of CDKs are measured for a tissue sampled from a patient, a characteristic of the tissue is determined by measurement data obtained, and it is then possible to make diagnosis of proliferation potency of cells contained in the tissue, sensitivity of cells contained in the tissue to anticancer agents, and malignancy of cancer of the tissue.

Proliferation potency as used herein refers to such information concerning whether or not control mechanism of proliferation is abnormal (presence or absence of canceration) at proliferative activity level of cells and ameuploid or the like.

Further, sensitivity to anticancer agent denotes presence or absence of effects for anticancer agent treatment. As for anticancer agents, for breast cancers, for example, CMF group (treatment administering concomitantly three agents of cyclophosphamide, methotrexate, and fluorouracil), taxane-based anticancer agents such as docetaxel, paclitaxel (or the like, CE (treatment administering concomitantly two agents of cyclophosphamide and epirubicin), AC (treatment administering concomitantly two agents of doxorubicin and cyclophosphamide), CAF (treatment administering concomitantly three agents of fluorouracil, doxorubicin and cyclophosphamide), FEC (treatment administering concomitantly three agents of fluorouracil, epirubicin and cyclophosphamide), treatment administering concomitantly two agents of transtuzumab and paclitaxel, capecitabine or the like are mentioned; for stomach cancer, for example, FAM (treatment administering concomitantly three agents of fluorouracil, doxorubicin and mitomycin C), FAP (treatment administering concomitantly three agents of fluorouracil, doxorubicin and cisplatin), ECF (treatment administering concomitantly three agents of epirubicin, cisplatin and fluorouracil), treatment administering concomitantly two agents of mitomycin C and tegafur, treatment administering concomitantly two agents of fluorouracil and carmustine, or the like are mentioned; for colon cancer, for example, treatment administering concomitantly two agents of fluorouracil and leucovorin, treatment administering concomitantly two agents of mitomycin and fluorouracil, or the like are mentioned; and for ovarian cancer, for example, TP (treatment administering concomitantly two agents of paclitaxel and cisplatin), TJ (treatment administering concomitantly two agents of paclitaxel and carboplatin), CP (treatment administering concomitantly two agents of cyclophosphamide and cisplatin), CJ (treatment administering concomitantly two agents of cyclophosphamide and carboplatin) are mentioned.

As for malignancy, specifically, revel of occurrence risk of metastasis development, prone to cancer recurrence and poor prognosis are mentioned. Recurrence means such cases where after the organ is resected in part for isolation of malignant tumor, the same malignant tumor recurs in the residual organ or where tumor cells are separated from the primary focus, carried to distant tissue (distant organ) and proliferate there autonomously (metastasis and recurrence). In general, a case where recurrence is recognized within five years is referred to as "prone to recurrence". According to stage level classification, stage III corresponds to recurrence rate 50% and is more liable to recurrence than stage II (recurrence rate 20%). Prognosis is to estimate a course of the disorder and termination, and the higher the mortality five years or ten years later, the worse the prognosis, and for example, mortality of stage III is 50% which is worse than stage II (20%).

The expression level and the activity are measured with more than two types of CDK, and ratio of these two (CDK specific activity expressed by the following equation or inverse number thereof) is obtained for every CDK to determine a characteristic of a tissue sampled from a patient.

CDK specific activity=CDK activity value/CDK expression level

The CDK specific activity calculated by above-shown equation corresponds to, of CDKs present in the cells, the percentage of CDKs showing activity and may be said to be CDK activity value based on proliferative state of cells contained in the tissue of determination object. From specific activity of more than two types of CDK, for example, ratio of specific activity of a first CDK (first CDK) to specific activity of a second CDK (second CDK), it is possible to know which CDK activity value is predominant and from this, it is possible to know the percentage of cells at a certain period of cell cycle and at which time of cell cycle the percentage of cells becomes dominant.

CDK as used herein is a collective term of group of enzymes being activated by binding to cyclin and is functioning at a specified period of the cell cycle depending on the type. Further, CDK inhibitor is a collective term of group of factors binding to cyclin-CDK complex thereby inhibiting activity thereof. In cells, CDK is normally present in the cytoplasm as an inactive type single substance and moves into nucleus when CDK per se is activated by phosphorylation or the like. In the nucleus, CDK binds to cyclin molecule present in the nucleus to become active type CDK, and regulates progression of cell cycle positively in various stages of the cell cycle. In the meantime, CDK inhibitor inactivates CDK by binding to CDK single substance or to active type CDK, thereby regulating progression of cell cycle negatively. Accordingly, in cells, CDK alone, complexes of CDK and cyclin and/or CDK inhibitor (hereinafter abbreviated as CDK group in some cases) are present eventually.

CDK, measurement object of the present reagent kit, is preferably selected from the group consisted of CDK1, CDK2, CDK4, CDK6, cyclin A-dependant kinase, cyclin B-dependant kinase, cyclin D-dependant kinase and cyclin E-dependant kinase. Cyclin A-dependant kinase is a CDK that exhibits activity after binding to cyclin A and at present, both CDK1 and CDK2 are known to be corresponding to this. Cyclin B-dependant kinase is a CDK that exhibits activity after binding to cyclin B and at present, CDK1 is known to be corresponding to this. Cyclin D-dependant kinase is a CDK that exhibits activity after binding to cyclin D and at present, both CDK4 and CDK6 are known to be corresponding to this. Cyclin E-dependant kinase is a CDK that exhibits activity after binding to cyclin E and at present, CDK2 is known to be corresponding to this.

It has been known at present that as shown in Table 7, these CDKs become cyclin-CDK complex (active type CDK) being bound to respective corresponding cyclin and activate specified period of the cell cycle shown in Table 7. For example, CDK1 binds to cyclin A or B, CDK2 binds to cyclin A or E, and CDK4 and CDK6 bind to cyclin D1, D2 or D3 to become active type. Meanwhile, CDK activity value may be inhibited by CDK1 shown in Table 7. For example, p21 hinders CDK1, 2, p27 hinders CDK2, 4, 6, and p16 hinders CDK4, 6.

TABLE 7

| CDK | Cyclin to be bound | CDK inihibitor to be bound | Action time of active type CDK |
|---|---|---|---|
| CDK4 | Cyclin D1 | p27 | G1 |
| CDK6 | Cyclin D2 | p16 | |
| | Cyclin D3 | | |
| CDK2 | Cyclin E | p27 | G1→S |
| CDK2 | Cyclin A | p21, p27 | S-phase |
| CDK1 | Cyclin A | p21 | G2→M |
| | Cyclin B | | |
| Cyclin A-dependant kinase | Cyclin A | p21 p27 | CDK1: G2→M CDK2: S-phase |
| Cyclin B-dependant kinase | Cyclin B | p21 | CDK1: G2→M |
| Cyclin D-dependant kinase | Cyclin D | p27 p16 | CDK4, 6: G1 |
| Cyclin E-dependant kinase | Cyclin E | p27 | CDK2: S-phase |

Figure 2:
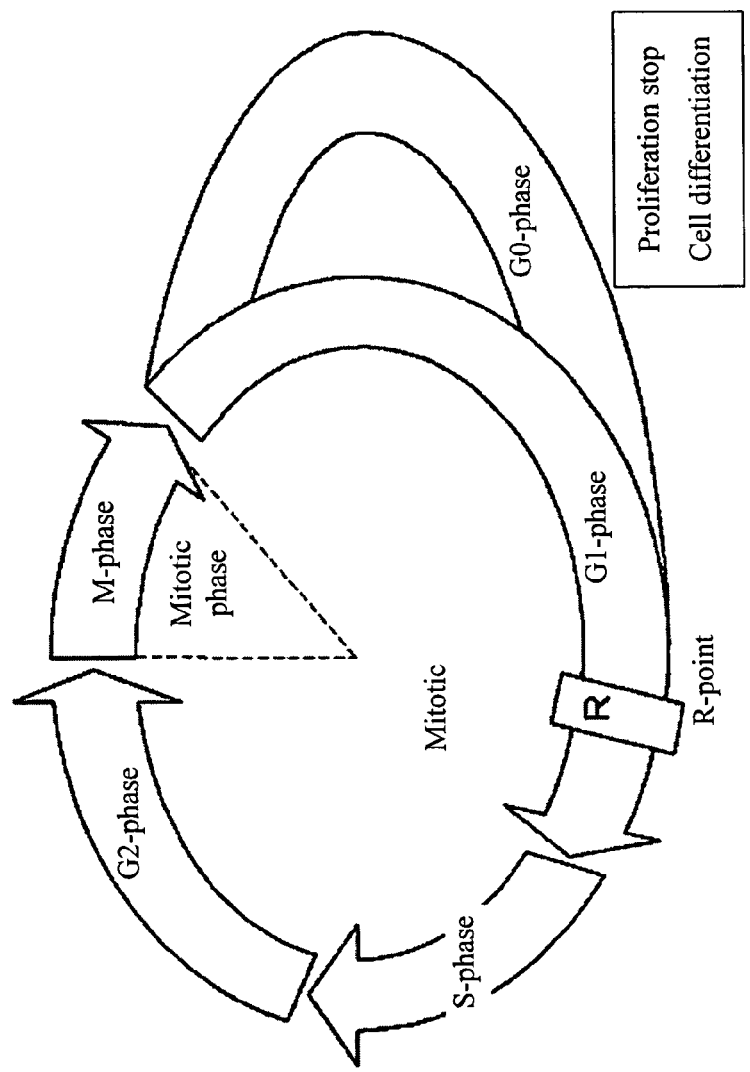
FIG. 2 is a drawing explaining cell cycle.

The cell cycle, in which cells initiate proliferation and return to the starting point in the form of two daughter cells through events such as DNA replication, chromosomal division, nuclear division, cytoplasmic fission or the like, is divided into four terms of G1-phase, S-phase, G2-phase and M-phase as shown in FIG. 2. S-phase is replication stage of DNA and M-phase is mitotic period. G1-phase is a period between completion of mitotic division and initiation of DNA synthesis which is a preparation and inspection period before entering into M-phase. After the critical point in G1-phase (R-point in animal cells), cell cycle starts and normally takes a round without cessation. G2-phase is a period between completion of DNA synthesis and initiation of mitotic division. Primary checkpoints of the cell cycle are immediately before entering from G1-phase into S-phase and inlet from G2-phase into mitotic division. Particularly, G1-phase checkpoint is an important step since it triggers initiation of S-phase. Because after a certain point of G1-phase, cells promote cell cycle in the order of S→G2→M→G1 without halting proliferation even without proliferation signal. Meanwhile, with cells which halted proliferation, there is an resting phase (G0) having DNA content of G1-phase, which is in a state outside the cell cycle. After a time period slightly longer than G1-phase of the cell cycle, it can proceed to S-phase by growth induction.

In general, it is considered that since cancer cells are proliferated actively beyond normal proliferation control, rate of cells in S-phase and G2-phase is high. Further, such cancers show rapid progress and are said to be malignant. It is believed that ameuploid takes place after elapsed abnormal M-phase or progressed into G1-phase and entered into S-phase without passing M-phase, that rate of cells existing in M-phase is low is an index to determine the malignancy. Therefore, if CDK1 that is activated and acting from G2-phase to M-phase is selected as the first CDK, and CDK2 that is activated and acting from G1-phase to S-phase is selected as the first CDK, as the measurement object of the expression level and the activity, and if ratio of specific activity obtained from the results of measurements is compared with a predetermined threshold value, these may be used as indexes of proliferation potency of cells and malignancy of cancer of cancers.

Besides, ratio of specific activity mentioned above may also be applicable to the sensitivity of cells for drugs. For example, a difference of therapeutic efficiency of drugs such as anticancer agents or the like depending on hereditary trait of patients, which is frequently cited in recent years, is attributable to a difference of sensitivity of cells for drugs. In other words, the characteristic possessed originally by cells includes such one whether or not cells have sensitivity for drugs, and ratio of specific activity of two types of CDK is also related to sensitivity for drugs. It is then possible to determine the sensitivity of cells for drugs by comparing the ratio of specific activity obtained from the results of measurements of the expression level and activity of two types of CDK with a predetermined threshold.

Detailed information of the method for determining a characteristic of a tissue and the method for determining sensitivity for drugs (anticancer agents) are described in International Publication No. WO2004/076686, Japanese Patent Application No. 2004-375639 (WO 2005/116241) and Japanese Patent Application No. 2005-158373 (US 2006/017363).

Although mammals, measurement objects of the present reagent kit, are not specifically limited, the present reagent kit is effective for humans, particularly clinical state, more particularly status of the cancer for which determination is necessary.

For sample tissue which is measurement object of the present reagent kit, those from which one desires to obtain pathological information, such as a tissue containing tumor cells where control mechanism of proliferation is abnormal are preferred. Further, the present reagent kit is preferably used for such a case where it is desired to obtain a guidance whether or not antitumor treatment be initiated considering physical and mental damages of the patient and expensive costs or the like incurred in promoting cancer therapy. For tissues, breast, lung, liver, stomach, large intestine, pancreas, skin, uterus, testis, ovary, thyroid gland, parathyroid gland, lymph system, bone marrow or the like are preferred tissues. For types of cancers, breast cancer, stomach cancer, colon cancer, esophageal cancer, prostate cancer or the like are mentioned.

The following description explains more concretely a method for determining malignancy of human cancers and efficacy (sensitivity) of anticancer agents based on results of measurements of the expression level and the activity value of cyclin-dependant kinase (hereinafter, abbreviated as CDK) contained in a tissue sampled from a patient using the reagent kit according to the present invention and the tissue characteristic determination apparatus capable mounting the reagent kit.

Figure 3:
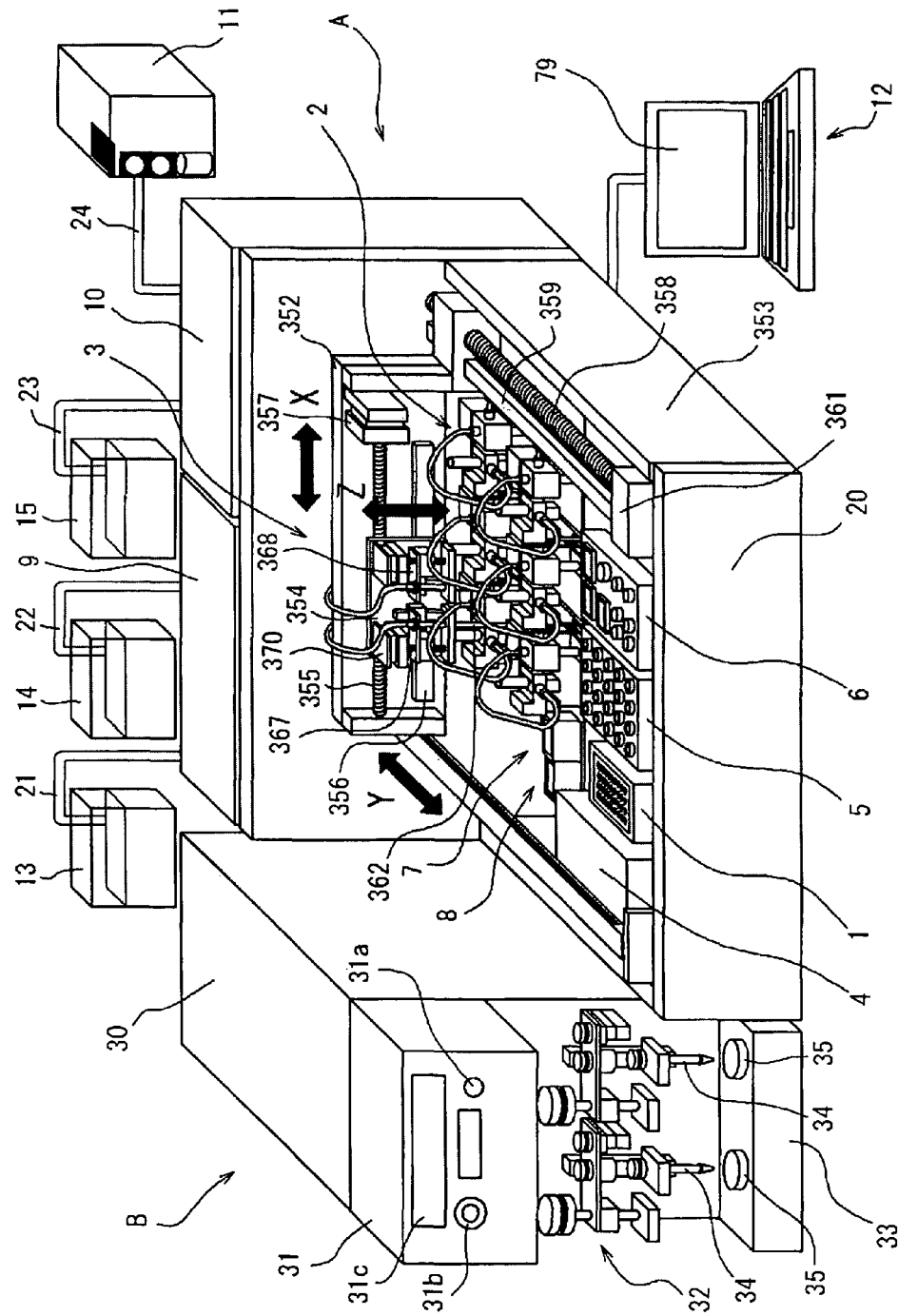
FIG. 3 is a perspective view showing a determination apparatus for determining a characteristic of a tissue carrying reagent kit of the embodiment according to the present invention.

First, the tissue characteristic determination apparatus will be explained. FIG. 3 is a perspective view showing tissue characteristic determination apparatus A capable of mounting the present reagent kit (hereinafter, referred to as determination apparatus A). The determination apparatus A primarily comprises a detection unit 4 disposed at front part of an apparatus body part 20, a chip set unit 1, a first reagent set unit 5 and a second reagent set unit 6, an activity measurement unit 2 disposed at rear part of the apparatus body part 20, a waste fluid bath 7 for accommodating waste fluids and a pipette washing bath 8 for washing pipette, a dispensing mechanism unit 3 disposed at upper part of the apparatus body part 20 and is capable of moving the pipette in three directions (X-direction, Y-direction and Z-direction), a fluid unit 9 and an electronic circuit board 10 disposed at rear part of the apparatus body part 20, and a personal computer 12 that is a control means and is communicably connected to said detection unit 4 and the electronic circuit board 10. Besides, a pure water tank 13, a washing solution tank 14, a waste fluid tank 15 and a pneumatic source 11 are provided to the determination apparatus A. The pure water tank 13 accommodates pure water for fluid path washing used upon completion of measurements and is connected by a piping 21 to a fluid unit 9, the washing solution tank 14 accommodates washing solution for pipette washing and is connected by a piping 22 to the pipette washing bath 8, and the waste fluid tank 15 for keeping the waste fluid is connected by a piping 23 to the waste fluid bath 7. Further, the determination apparatus A is also provided with a solubilization apparatus B for obtaining from a tissue measurement samples capable of being processed by the determination apparatus A.

The solubilization apparatus B is to prepare, prior to processing by the determination apparatus A, samples in liquid state capable of being processed by the determination apparatus A from a tissue, and comprises a chassis unit 30, an operation unit 31 disposed at front upper part of the chassis unit 30, a driving unit 32 equipped with a pair of pestles 34 for pressing and grinding said tissue, and a sample set unit 33 to which an Eppendorf tube 35 for accommodating said tissue is set.

The driving unit 32 moves the pestle 34 up/down and is capable of generating rotational movement, by which movement biological samples filled into the Eppendorf tube 35 are being pressed and ground. In said chassis unit 30, a control unit (not shown) for controlling operations of such driving unit 32 is incorporated.

On the operation unit 31 are disposed an operation button 31a, an operation lamp 31b, and a display unit 31c for displaying status of the apparatus, error messages or the like. Further, a cooling means (not shown) is disposed within the sample set unit 33 by which temperature of the biological samples in the Eppendorf tube being set at recessed part on upper surface of the sample set unit 33 is maintained constant. The biological sample is solubilized by the solubilization apparatus B and subjected to centrifugation by a centrifugal machine (not shown), and supernatant solution thereof is sampled into a predetermined sample container and is set to the first reagent set unit 5 of the determination apparatus A.

With a similar manner as the sample set unit 33, a cooling means (not shown) is disposed in the first reagent set unit 5 to maintain temperatures of the samples in a container such as screw cap or the like to be set at recessed part on upper surface of the first reagent set unit 5, various fluorescent label CDK antibody solutions, various CDK antigen solutions or the like constant. The tissue characteristic determination apparatus used in the embodiment is designed to have a total of 20 recessed parts (longitudinally five rows, laterally four rows) so that maximum 20 containers such as screw caps or the like may be set.

The second reagent set unit 6 is disposed next to the first reagent set unit 5. A plurality of recesses are formed in the second reagent set unit 6 likewise the first reagent set unit 5, and Eppendorf tubes containing buffer, substrate solution, fluorescent enhancement reagent or the like, and containers such as screw caps or the like are set in these recesses. Prior to processing by the determination apparatus A, chip set for measurement is set to the chip set unit 1 and at the same time, a column is set to the activity measurement unit 2.

Figure 4:
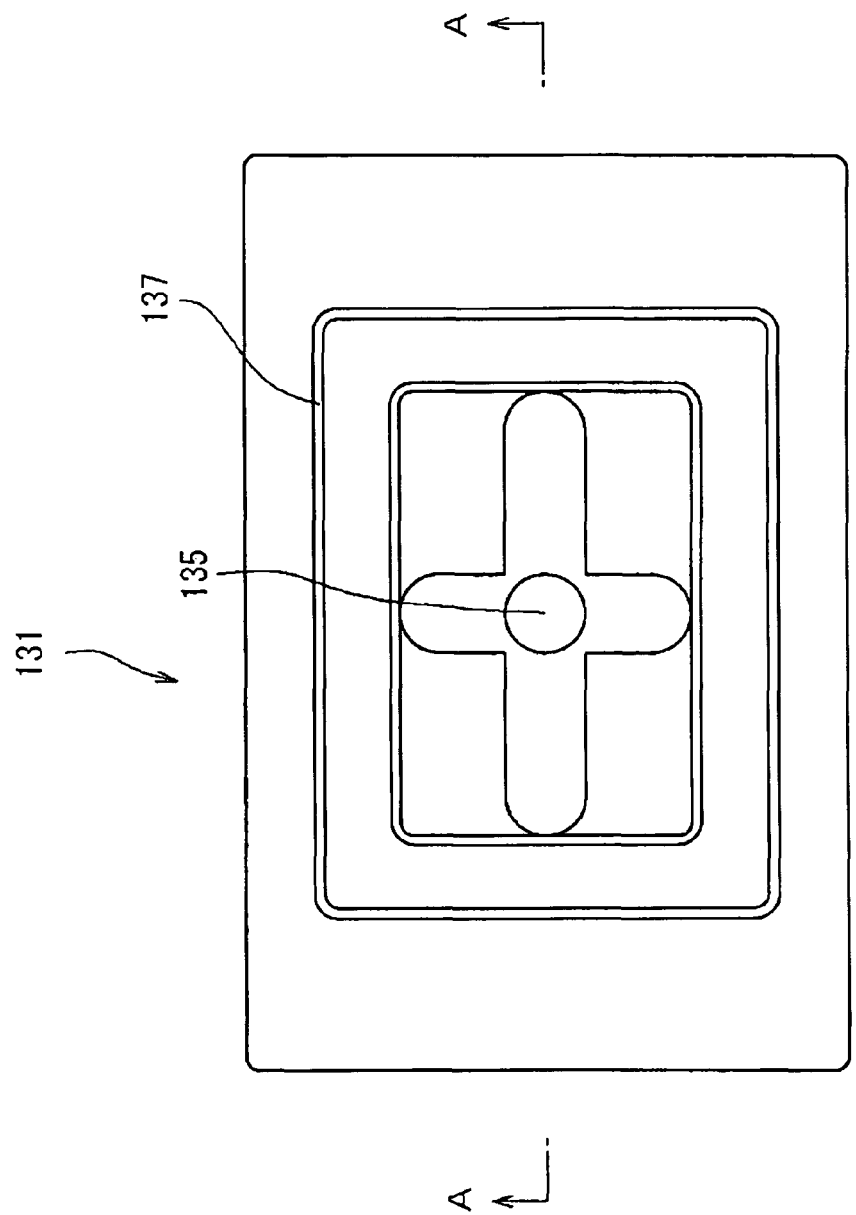
FIG. 4 is a top view of chip set portion in the determination apparatus shown in FIG. 3.
Figure 5:
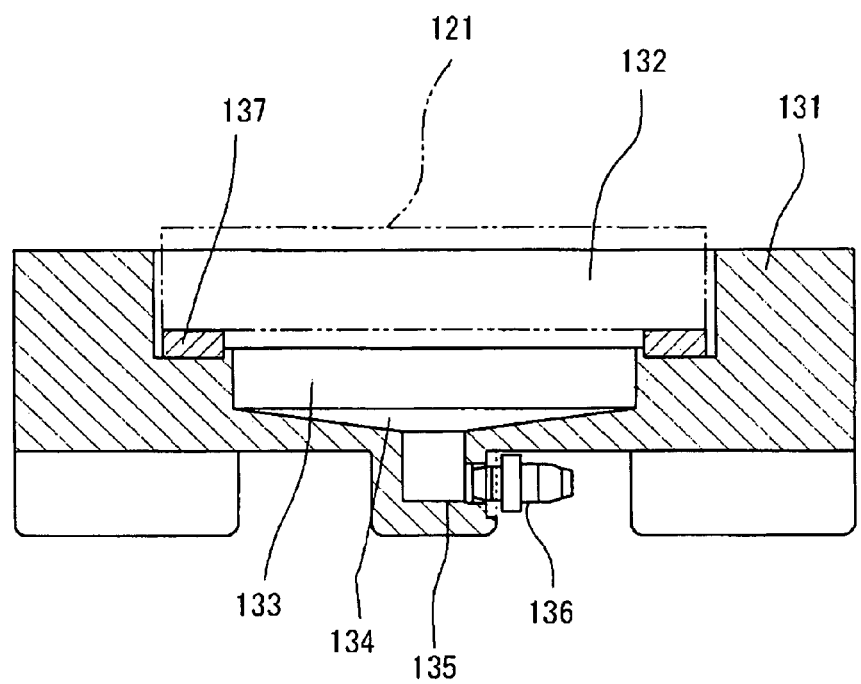
FIG. 5 is A-A sectional view of FIG. 4.

The chip set unit 1 is consisted of aluminum blocks, has a recess 132 for loading the measurement chip 121 at upper surface as shown in FIGS. 4 to 5 and also has a suction port 135 at the bottom. More specifically, the chip set unit 1 is equipped with the first recess 132 in rectangular shape at upper surface and a second recess 133 also in rectangular shape at the bottom surface of the first recess 132. At the bottom of the first recess 132, an elastic gasket 137 made of rubber in rectangular frame shape is disposed around periphery of the second recess 133.

The second recess 133 is equipped with a groove 134 in cross shape at the bottom thereof and the suction port 135 at the bottom center, and at the bottom of the groove 134, an inclination is provided from periphery of the second recess 133 deepening towards the center. The suction port 135 is communicated with a nipple 136 provided to allow connection with an external suction pump (not shown). The measurement chip 121, which will be dealt with later, is then loaded horizontally via a bottom gasket 137 of the first recess 132. After a sample solution containing proteins is filled or dropped into each of wells of the measurement chip 121, the suction pump (not shown) connected to the nipple 136 starts operation. Following this, the measurement chip 121 is adsorbed to the bottom of the first recess 132 via the gasket 137 in a sealed manner and at the same time, sample solution in each of wells is sucked via hydrophobic porous membrane, which will be dealt with later, and proteins of the measurement object are solid-phase formed to the membrane. In this case, a fixing member for pressing the measurement chip 121 against the bottom of the first recess 132 for fixing purpose may be provided in the chip set unit 1.

The measurement chip 121 is consisted of an upper template 101 and a lower template 111 to grasp hydrophobic porous membrane 122 and hydrophobic porous membrane 122 (sectional view is shown in FIG. 10). This protein solid phase chip 121 serves as a second contact means to cause a contact of antibody solution containing cyclin-dependant kinase antibody with a sample. For the hydrophobic porous membrane 122, Immobilon-FL (PVDF membrane, pore size 0.45 μm) supplied by Millipore was used.

Figure 6:
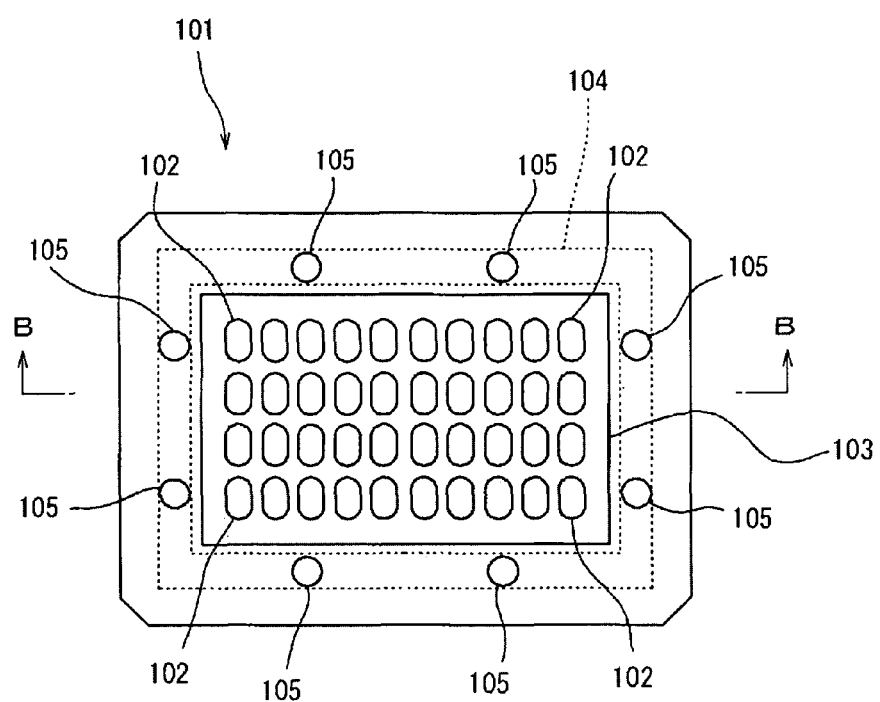
FIG. 6 is a top view of upper template for protein solid phase chips to be set to chip setting unit in the determination apparatus shown in FIG. 3.
Figure 7:
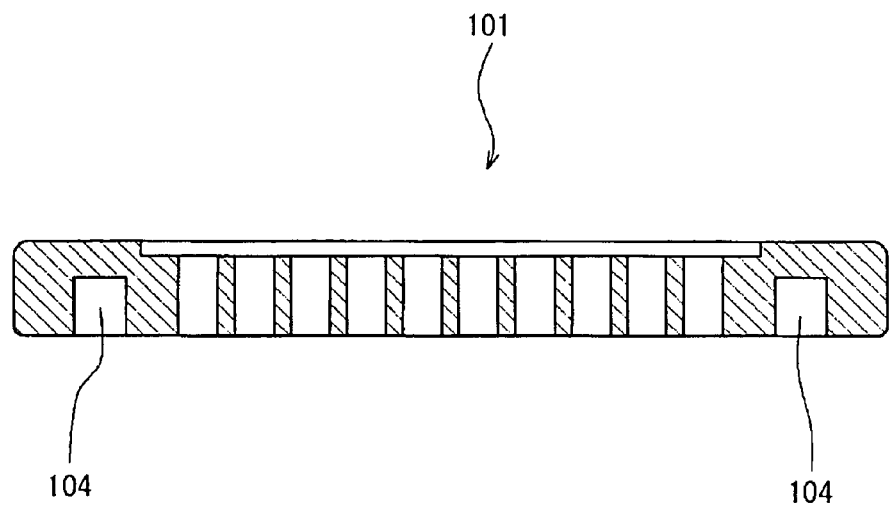
FIG. 7 is B-B sectional view of FIG. 6.

The upper template 101 is shown in FIGS. 6 to 7. Forty rectangular penetration holes 102 are punched to the upper template 101 of rectangular plate shape being disposed in 4-lines×10-rows in matrix configuration. A groove (recess) 104 running around periphery of said 40 penetration holes 102 are formed at lower surface of the upper template 101. A rectangular hydrophobic porous membrane mounting area 103 is sectioned by this groove 104 inside thereof. Further, eight jig penetration holes 105 are punched at the bottom of the groove 104.

Figure 8:
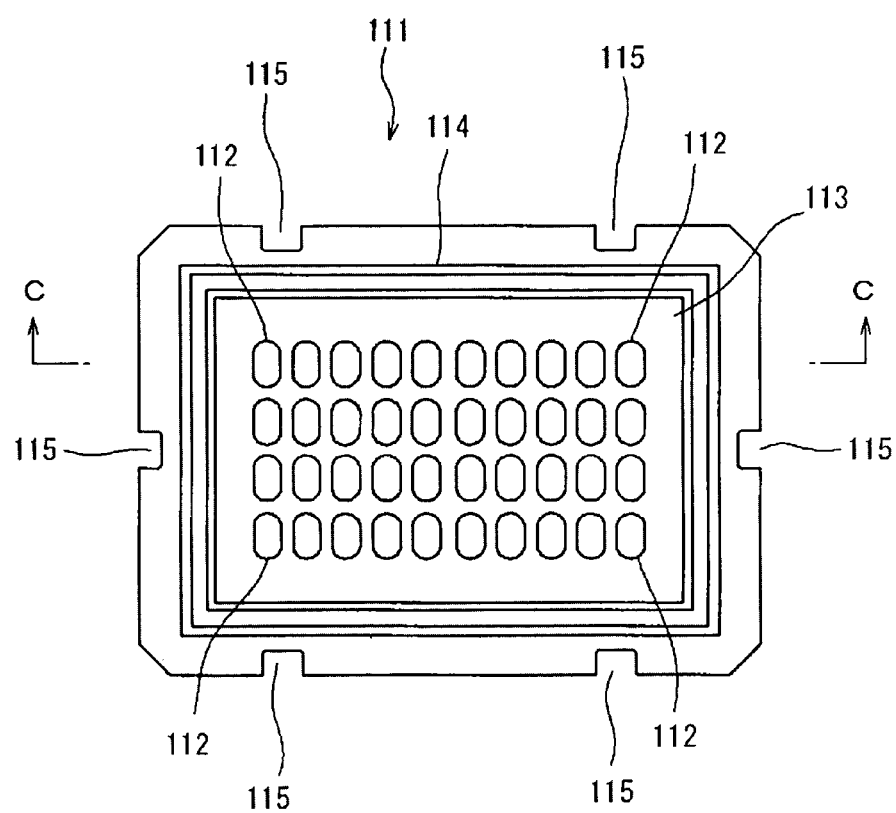
FIG. 8 is a top view of lower template for protein solid phase chips to be set to chip setting unit in the determination apparatus shown in FIG. 3.
Figure 9:
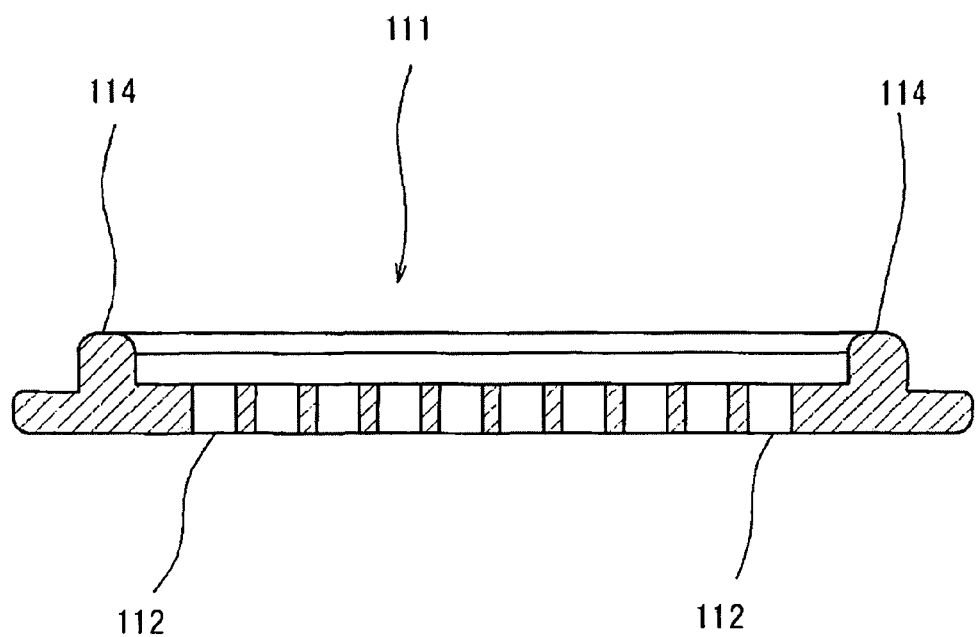
FIG. 9 is C-C sectional view of FIG. 9.

Meanwhile, forty oval penetration holes 112 are formed to the lower template 111 of rectangular plate shape shown in FIGS. 8 to 9 being disposed in 4-lines×10-rows in matrix configuration corresponding to penetration holes 102 on said upper template 101. The penetration holes 112 have same profile and sectional area as the penetration holes 102.

A convex part 114 on a ridge running around periphery of 40 penetration holes 112 is formed on the upper surface of the lower template 111 at the position corresponding to said groove 104. A rectangular hydrophobic porous membrane mounting area 113 is sectioned by this convex part 114 inside thereof. Six notched parts 115 are formed to the rim of the lower template 111. Meanwhile, the upper template 101 and the lower template 111 may be configured by, for example, vinyl chloride resin.

FIG. 10 shows sectional view of the measurement chip 121, where the upper template 101 and the lower template 111 are overlapped as illustrated. The convex part 114 is detachably pressed in to the groove 104 thereby allowing each of penetration holes 102 and each of penetration holes 112 to become coaxial with each other. When used, the rectangular hydrophobic porous membrane 122 is loaded between the hydrophobic porous membrane mounting areas 103 and 113, and is compressed uniformly by pressing in of said convex part 114 into the groove 104. With this consideration, the hydrophobic porous membrane 122 is sectioned by each of penetration holes 102 in watertight manner, and wells (liquid reservation) as many as the number of the penetration holes 102 are formed.

Figure 11:
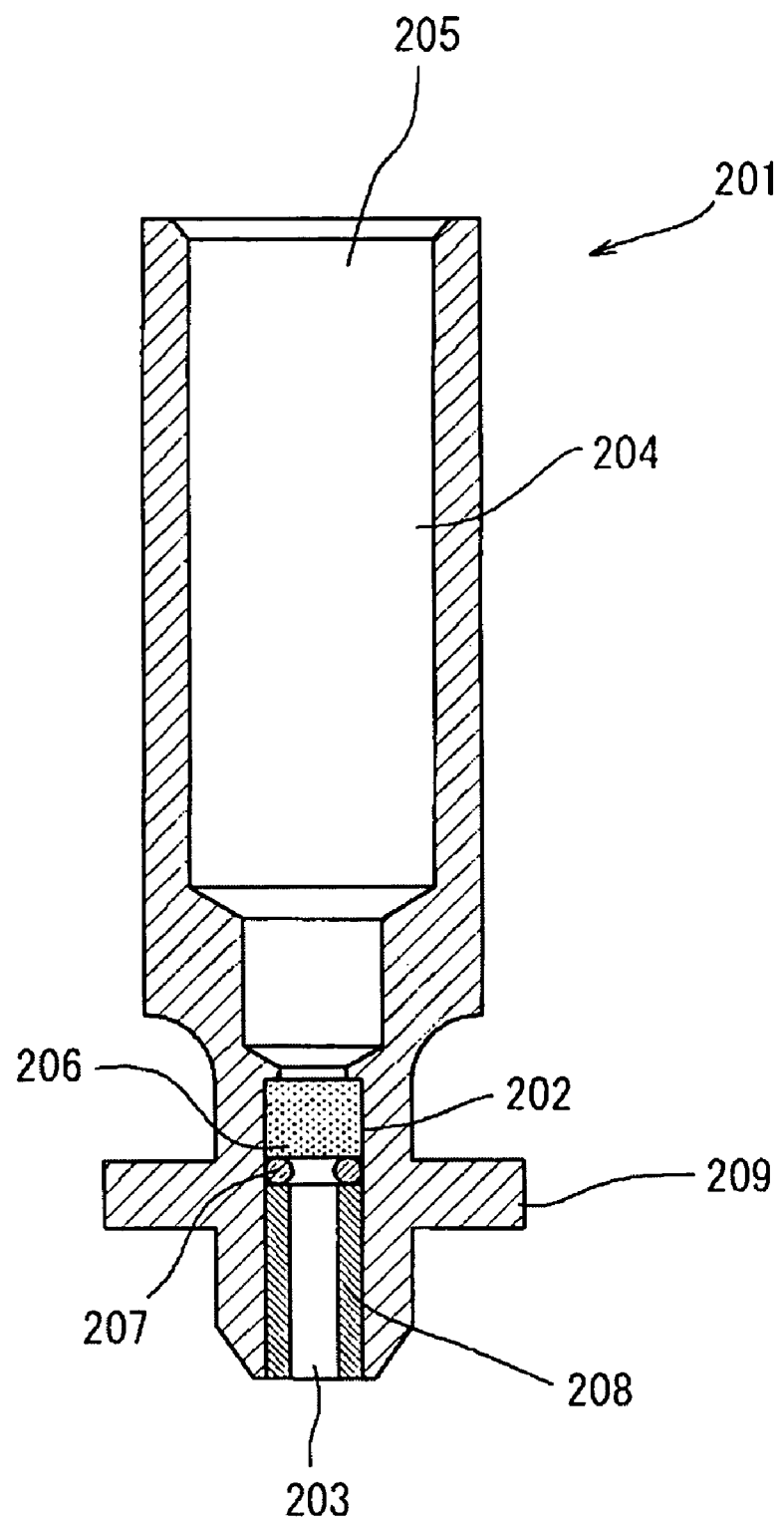
FIG. 11 is a sectional view explaining column at sample preparation unit of activity measurement unit in the determination apparatus shown in FIG. 3.

As shown in FIGS. 11 to 14, the activity measurement unit 2 is consisted of a plurality of sample preparation units 211 each equipped with a column 201 and a fluid manifold 213, and is used for measurements of CDK activity value. The column 201 shown in FIG. 11 is consisted of a cylindrical body made of vinyl chloride resin and has therein a carrier retainer 202 for retaining a carrier 206 that is used for isolation of target materials in the liquid sample, and a liquid reservation part 204 for receiving and accumulating the liquid sample by this carrier retainer 202. The column 201 constitutes a first contact means for causing contact of substrate solution containing a predetermined substrate with the sample.

The liquid reservation part 204 of the column 201 is equipped with an opening 205 at upper part from which liquid sample can be filled or sampled from the outside. In order to trap CDK1 or CDK2 in liquid sample, the carrier 206 is consisted of monolith silica gel in cylindrical shape to which is immobilized CDK1 or CDK2 antibody. This monolith silica gel has, different from particle carrier, three-dimensional network-like framework with monolithic voids. The carrier 206 is inserted from lower opening of the column 201 to the carrier retainer 202 and is supported being biased elastically by a fixing pipe 208 via O-ring 207. Meanwhile, the fixing pipe 208 is pressed in from lower opening of the column 201 and a hole of the fixing pipe 208 and of the O-ring 207 form a liquid introduction part 203.

Figure 12:
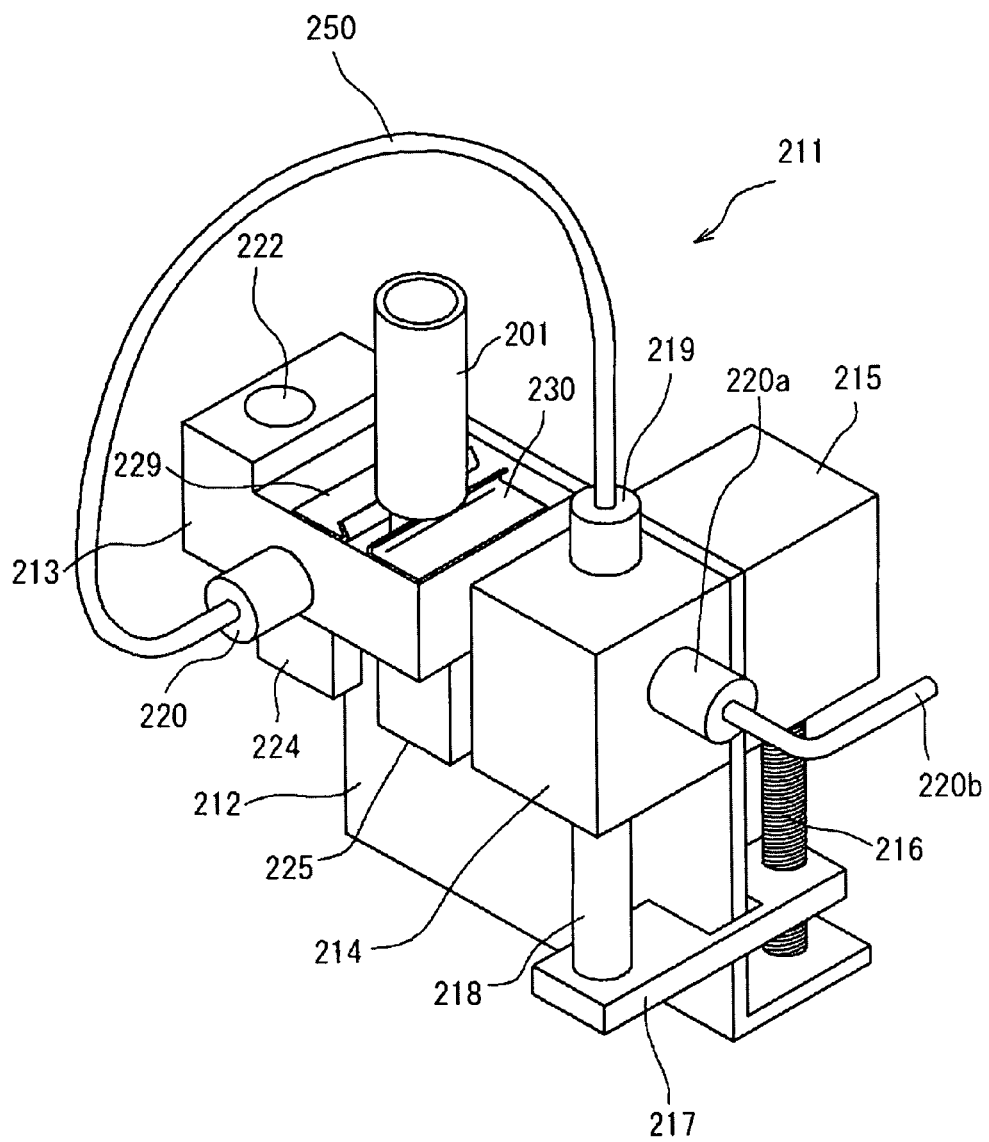
FIG. 12 is a perspective view showing sample preparation unit of activity measurement unit of the determination apparatus shown in FIG. 3.

Besides, a loading flange 209 for loading and fixing the column 201 to the sample preparation unit 211 is formed at the lower end of the column 201. This flange 209 is an oval type flange being formed by cutting both ends of a disk-shaped flange having diameter D to obtain width W (W<D). FIG. 12 is a perspective view showing the sample preparation unit 211 and as shown in the drawing, the sample preparation unit 211 is equipped with an L-shaped supporting plate 212, and to this supporting plate 212 are fixed a fluid manifold 213, a syringe pump 214 and a stepping motor 215 with reduction gear.

A screw shaft 216 is connected to output shaft of the stepping motor 215. A driving arm 217 threaded to the screw shaft 216 is connected to front edge of a piston 218 of the syringe pump 214. It is designed that when the screw shaft 216 is turned by the stepping motor 215, the piston 218 moves up/down. The syringe pump 214 and the fluid manifold 213 are connected by a liquid transfer tube 250 via connectors 219, 220. Further, the syringe pump 214 is connected to a chamber 234 (FIG. 14) accommodating liquid (washing solution) for fulfilling the flow path by a liquid transfer tube 220b via connector 220a.

Figure 13:
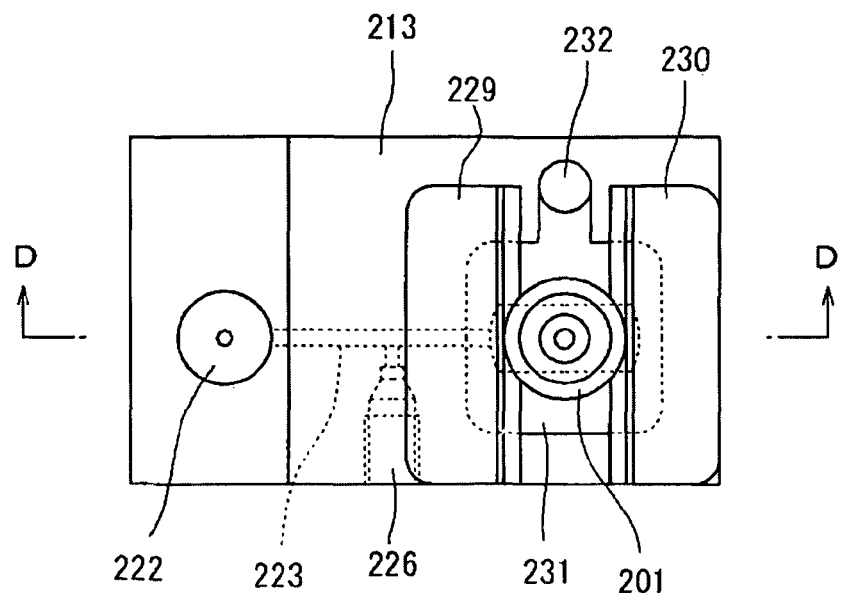
FIG. 13 is a top view of fluid manifold of the sample preparation unit shown in FIG. 12.
Figure 14:
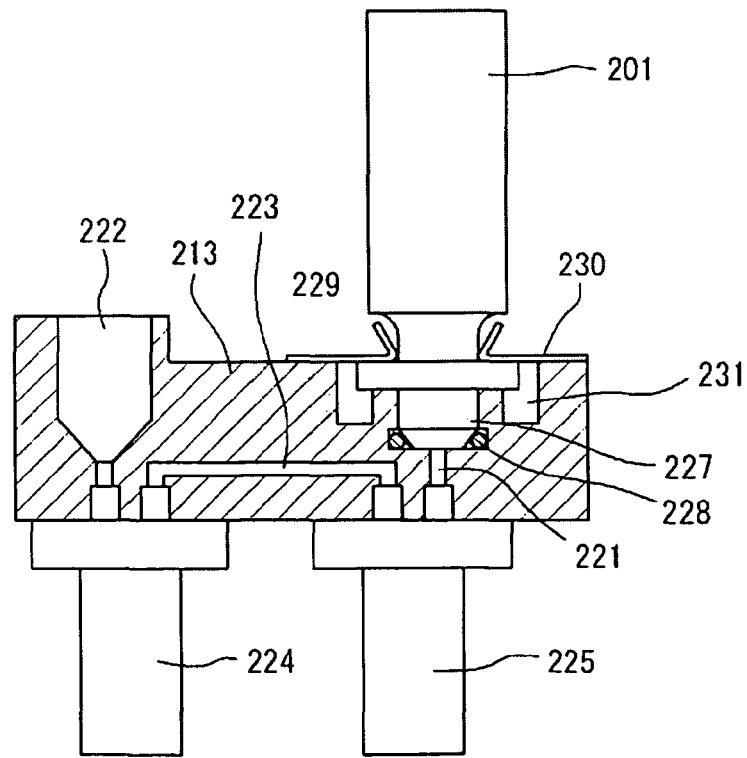
FIG. 14 is D-D sectional view of FIG. 13.

As shown in FIGS. 13 to 14, the fluid manifold 213 is equipped with a column connection part 221 to which is connected a liquid introduction part 203 of the column 201, and a liquid sample receiving part 222 for receiving liquid sample. The fluid manifold 213 is equipped with a flow path 223 therein and is equipped with at lower surface thereof an electromagnetic valve 224 for opening and closing between a liquid receiving part 222 and the flow path 223, an electromagnetic valve 225 for opening and closing between the flow path 223 and the column connection part 221. Further, the fluid manifold 213 has a screw hole 226 for connector connection for connecting a connector 220 to side face, and this screw hole 226 is connected to the flow path 223.

Figure 15:
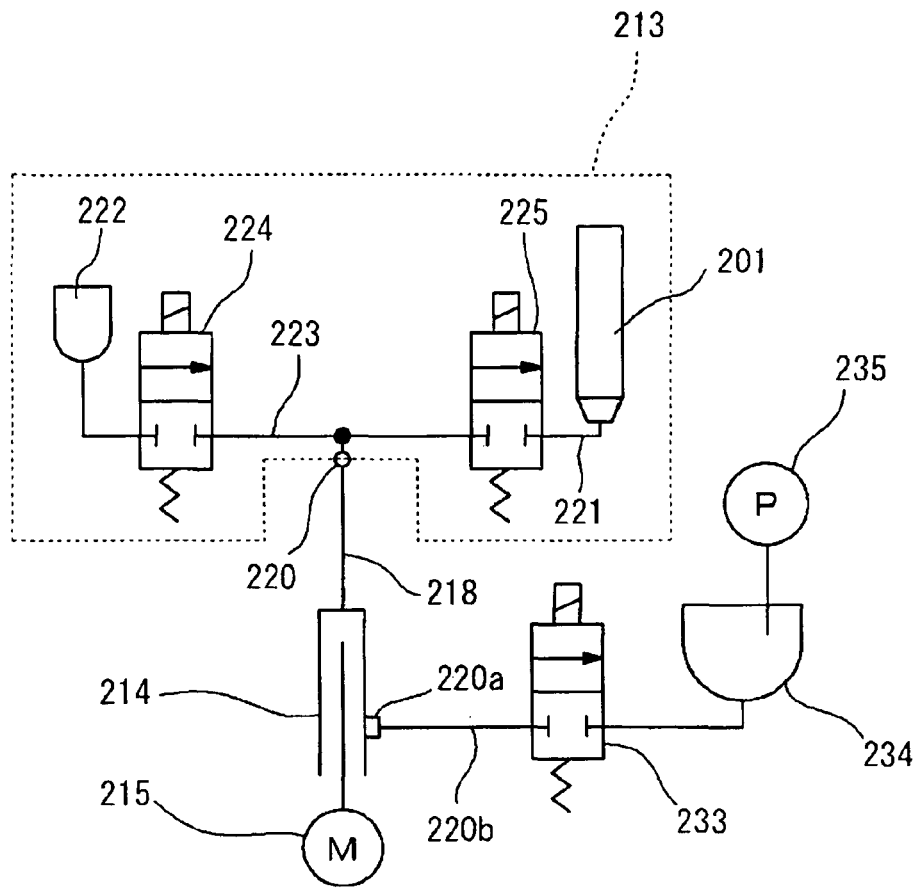
FIG. 15 is a fluid circuit diagram of the sample preparation unit shown in FIG. 12.

FIG. 15 is a fluid circuit diagram of the sample preparation unit 211 showing a state where the syringe pump 214 is connected to the fluid manifold 213 via the connector 220a. The chamber 234 is connected to the syringe pump 214 via an electromagnetic valve 233 and positive pressure is applied from a positive pressure source 235 to the chamber 234.

Here, a method for loading the column 201 to the fluid manifold 213 will be explained. As shown in FIGS. 13 to 14, a column receiving recess 227 for receiving lower end of the column 201 is formed at upper surface of the fluid manifold 213, center of the bottom of this recess 227 penetrates the column connection part and at the same time, an O-ring 228 is mounted around circumference of the bottom. Further, two presser plates 229, 230 with L-shaped section are fixed in parallel to upper surface of the fluid manifold 213 around the column loading recess 227 with a distance broader than said width W and intervals narrower than said D.

Then, the column 201 is loaded to the column loading recess 227 so that the flange 209 passes between presser plates 229, 230, and is turned clockwise or counterclockwise by 90 degrees. With this manipulation, diameter D portion of the flange 209 is engaged with the presser plates 229, 230, and the flange 209 is fixed to the presser plates 229, 230 by elasticity of the O-ring 228. When removing the column 201, it is simply turned in either right or left by 90 degrees while the column 201 is being held.

The recess 227 of the fluid manifold 213 is filled with fluid to prevent entry of air bubbles when the column 201 is loaded to the fluid manifold 213 of the sample preparation unit 211. However, when front edge of the column 201 is inserted to the recess 227, the fluid will spill over due to its volume. In order to prevent this liquid from flowing to the periphery, a spill liquid reservation recess 231 is provided around the column loading recess 227, and a spill liquid draining recess 232 for suction draining of spill liquid using a pipette is provided at one portion of the spill liquid reservation recess 231. Various samples and reagents are filled or sucked to or from a predetermined place by the dispensing mechanism unit 3 equipped with a pipette. Here, operations taken when a sample or reagent is filled to the liquid sample receiving part 222 will be explained. When a sample or reagent is filled to the liquid sample receiving part 222, first, the electromagnetic valve 224 is opened (electromagnetic valves 225 and 233 are closed) and the syringe pump 214 starts suction operation. Then the sample or reagent is passed through the electromagnetic valve 224 and is sucked to the syringe pump 214 side. Second, the electromagnetic valve 224 is closed and the electromagnetic valve 225 is opened, and the syringe pump 214 starts discharge operation. By these operations, the sample or reagent is passed through the electromagnetic valve 225 and is delivered in the column 201.

As shown in FIG. 3, the dispensing mechanism unit 3 is equipped with a frame 352 for pipette movement in X-direction, a frame 353 for pipette movement in Y-direction, and a plate 354 for pipette movement in Z-direction. The frame 352 is equipped with a screw shaft 355 for movement of the plate 354 in X-direction shown by an arrow, a guide bar 356 for supporting and sliding movement of the plate 354, and a stepping motor 357 for turning the screw shaft 355. The frame 353 is equipped with a screw shaft 358 for movement of the frame 352 in Y-direction shown by an arrow, a guide bar 359 for supporting and sliding movement of the frame 352, and a stepping motor 361 for turning the screw shaft 358. Further, the plate 354 is equipped with a screw shaft 367 for movement of an arm 368 supporting a pipette 361 in Z-direction shown by an arrow, a guide bar for supporting and sliding movement of the arm 368, and a stepping motor 370 for turning the screw shaft 367.

With the tissue characteristic determination apparatus used in the configuration of the embodiment, the dispensing mechanism unit 3 is equipped with a pair of pipettes 362 and therefore, reagents or the like can be filled simultaneously into two sample containers or contents can be sucked simultaneously from two sample containers, thereby ensuring efficient measurement processings.

As shown in FIG. 3, to the rear part of the apparatus body part 20 is disposed a fluid unit 9 which is connected to said pipette 362, a pipette washing bath 8, and each sample preparation unit 211 or the like for operations of the fluid. As shown in FIG. 14, this fluid unit 9 is equipped with electromagnetic valves 224, 225 of each sample preparation units 211, an electromagnetic valve 233 for controlling the fluid when charging liquid from low-temperature liquid chamber to the syringe 214, an electromagnetic valve for controlling the fluid at suction and discharge of the liquid by the pipette 362, an electromagnetic valve for controlling the fluid for suction of the liquid discarded from the pipette 362 in the waste fluid bath 7, and an electromagnetic valve for controlling the fluid when the pipette 362 is washed in the pipette washing bath 8.

Besides, to the rear part of the apparatus body part 20 are disposed various sample preparation units 211, stepping motors 357, 361, 370, the electronic circuit board 10 for supplying driving signals to fluid unit 9 or the like.

The detection unit 4 is to determine the amount of fluorescent material reflecting the amount of proteins solid-phased to the hydrophobic porous membrane 122 of the measurement chip 121 and of fluorescent material reflecting the amount of phosphate group, irradiates exciting light to the measurement chip 121, detects the amount of fluorescence generated, and outputs an electric signal with magnitude corresponding to the intensity of fluorescence detected to the electronic circuit board 10. As for the detection unit 4, those consisted of generally used light source unit, illumination system and light receiving system may be used appropriately.

Figure 16:
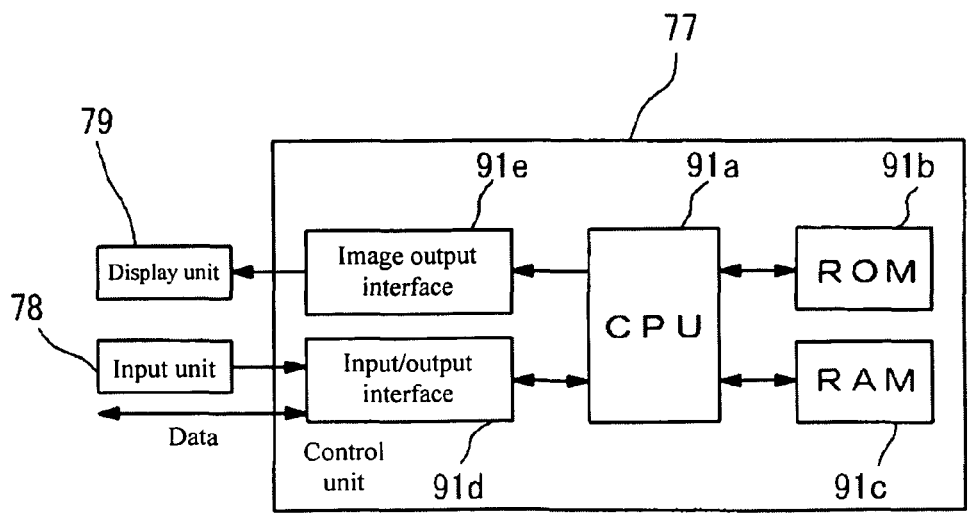
FIG. 16 is a block diagram showing hardware configuration of the control means.

The personal computer 12 which serves as the control means is, as shown in FIG. 16, consisted of a control unit 77 connected to said electric/electronic circuit board 10, an input unit 78 for inputting data or the like to the control unit 77, and a display unit 79 for displaying results of analysis or the like. The control unit 77 constitutes a first (second) expression level acquisition means for acquiring expression level from fluorescence intensity using analytical means and calibration curve, and a first (second) activity acquisition means for acquiring activity value from fluorescence intensity using calibration curve.

The control unit 77 is, as shown in FIG. 16, equipped with CPU91a, ROM91b, RAM91c, input/output interface 91d, and image output interface 91e. In the ROM91b are stored operating system, control program for controlling operation of the apparatus, and data necessary for execution of the control program. The CPU91a is capable of loading the control program to the RAM91c or executing directly from the ROM91b. Thus, data as a result of processing by the CPU91a are transmitted to the electronic circuit board 10 via input/output interface 91d, and data necessary for processing of the CPU91a are received from the electronic circuit board 10 via input/output interface 91d. By executing the control program, the CPU91a is now able to control the electronic circuit board 10. Further, the CPU91a acquires expression level and activity value of cyclin-dependant kinase (CDK) based on fluorescent intensity obtained by the detection unit 4 and acquires information on a characteristic of the tissue based on the values obtained. In order to acquire expression level and activity value of CDK, calibration curve, that serves as conversion data for converting fluorescence intensity into expression level or activity value, is stored in said RAM91c.

Figure 17:
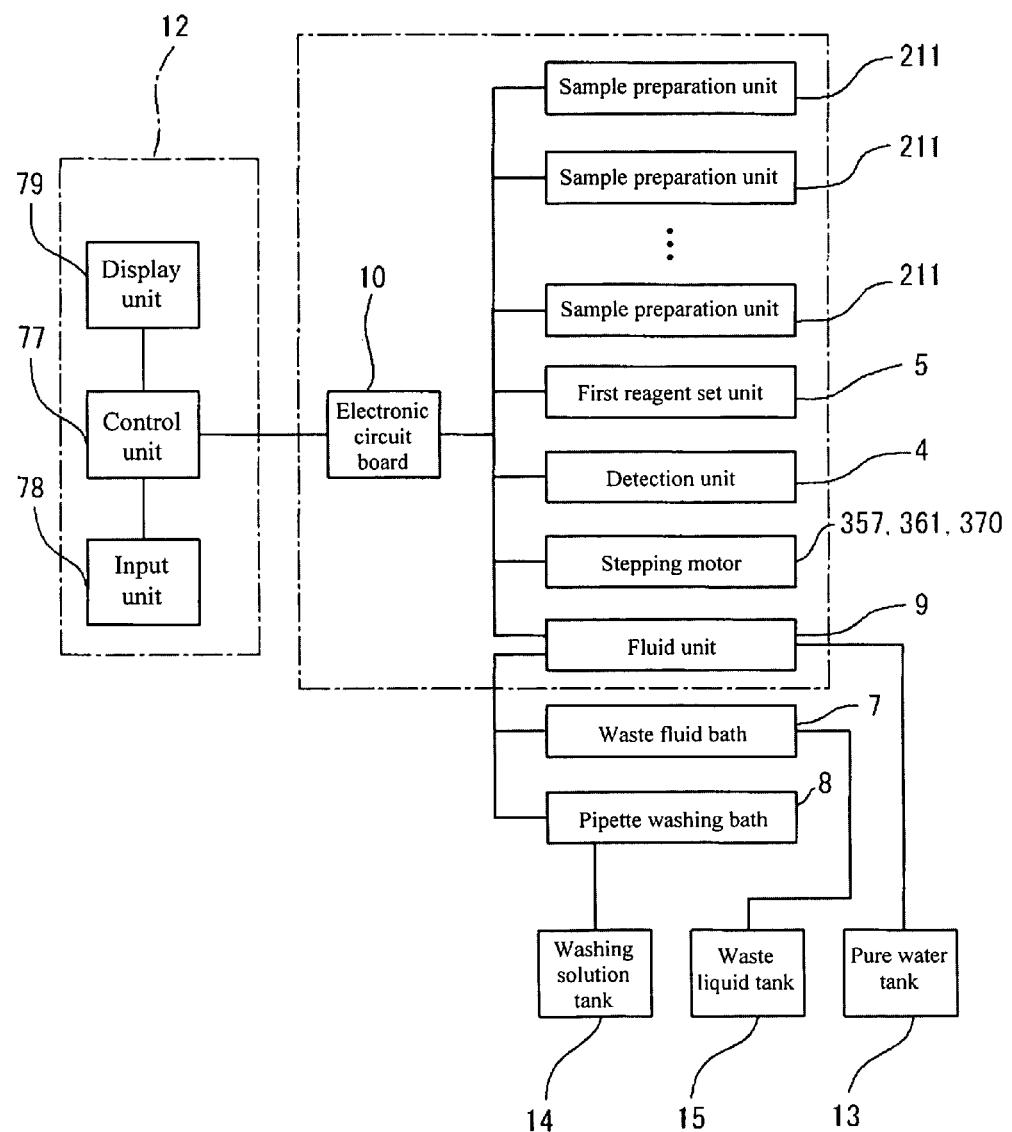
FIG. 17 is a block diagram showing control system for controlling the determination apparatus.

FIG. 17 is a block diagram showing control system for controlling the determination apparatus A. This control system is consisted of, as shown in the drawing, the electronic circuit board 10 having a driver circuit for driving each part of the dispensing mechanism unit 3, the control unit 77 for controlling the electronic circuit board 10 and for analyzing results of detection from the detection unit 4, the input unit 78 for inputting data or the like to the control unit 77, and the personal computer 12 consisted of the display unit 79 for displaying results of analysis or the like analyzed by the control unit 77.

By controlling the electronic circuit board 10, the control unit 77 outputs, from the electronic circuit board 10, a driving signal for driving the stepping motor 215 of each sample preparation units 211, a driving signal for temperature control of the first reagent set unit 5, a driving signal for driving stepping motors 357, 361, 370, and a driving signal for driving the electromagnetic valve provided in the fluid unit 9. Further, the control unit 77 takes in a detection signal from the detection unit 4 via the electronic circuit board 10.

Subsequently, a method for determining a characteristic of a tissue using the reagent kit and the determination apparatus A will be explained. Explanation will be given for a case where malignancy (level of recurrence risk) of human cancer cells and efficacy (sensitivity) of anticancer agents are determined. Meanwhile, reagent numbers used hereunder correspond to those shown in Table 1 to 6.

(1) Pretreatment by Solubilization Apparatus

Prior to treatment by the determination apparatus A, a method for collecting samples in liquid state from the tissue excised from cancer patient using the solubilization apparatus B will be explained. First, using a pincette, a tissue excised from the cancer patient (approximately 2 mm$^3$) was put into a test tube containing tissue solubilization solution (Reagent No. 3001), and this test tube was set to the sample set unit 33 of the solubilization apparatus B shown in FIG. 3. Then, by pressing the start button of the operation unit 31, the pestle 34 moves down to a predetermined position and presses the tissue in the test tube against bottom of the test tube. In this state, the pestle 34 was turned to grind the tissue. Driving of the pestle 34 was stopped after a predetermined time, the pestle was moved upwardly and then the test tube was taken out from the sample set unit 33. Contents of the test tube solubilized were subjected to centrifugation and a supernatant solution thus obtained was sampled manually.

(2) Setting of Expression Measurement Sample to Determination Apparatus

The supernatant solution obtained was put into two sample containers, diluted by dilution rates different each other, and were set to a predetermined position of the first reagent set unit 5. Of two samples, one is for expression level measurement and the other is for activity measurement.

Further, fluorescent labeled CDK1 antibody solution (Reagent No. 1001), fluorescent labeled CDK2 antibody solution (Reagent No. 1002), fluorescent labeled p21 antibody solution (Reagent No. 1003), fluorescent labeled GAPDH antibody solution (Reagent No. 1004), CDK1 antigen solution 1 (Reagent No. 1005), CDK1 antigen solution 2 (Reagent No. 1006), CDK2 antigen solution 1 (Reagent No. 1007), CDK2 antigen solution 2 (Reagent No. 1008), p21 antigen solution 1 (Reagent No. 1009), p21 antigen solution 2 (Reagent No. 1010), GAPDH antigen solution 1 (Reagent No. 1011), GAPDH antigen solution 2 (Reagent No. 1012), and calibrator solution for activation (Reagent No. 2011) were set to a predetermined position of the first reagent set unit 5.

Further, blocking solution (Reagent No. 1013), immunoprecipitation (IP) buffer (Reagent No. 2004), before reaction buffer 1 (Reagent No. 2005), before reaction buffer 2 (Reagent No. 2006), substrate solution (Reagent No. 2007), fluorescent labeled solution (Reagent No. 2008), fluorescent enhanced reagent (Reagent No. 2009), and reaction stopper (Reagent No. 2010) were set to a predetermined position of the second reagent set unit 5.

(3) Flow of Entire Processing by Determination Apparatus

Figure 18:
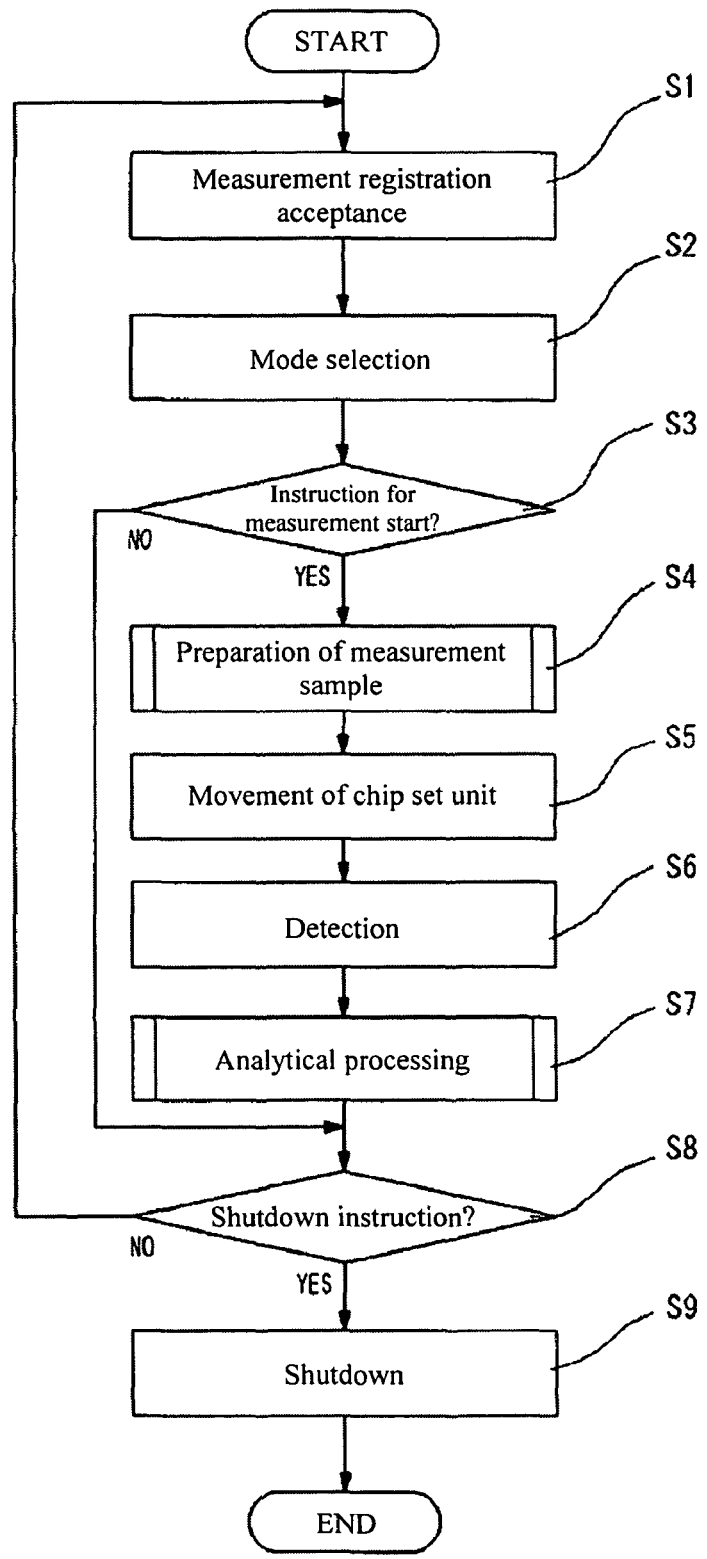
FIG. 18 is a drawing showing entire flow of processings by the determination apparatus.

Flow of entire processing by determination apparatus shown in FIG. 18 will be explained hereunder. When [Yes] and [No] are not shown in for judgment in the flowchart, downward arrow denotes Yes and right (left) arrow denotes No. Processings explained below are all controlled by the control unit 77.

Upon turning ON the power, processing for accepting measurement registration (step S1) is executed. With this processing, entry of information relating to the measurement such as sample number or the like is accepted. Next, processing for accepting measurement mode of either prognostic prediction mode (mode under which malignancy of human cancer cell (level of recurrence risk) is judged) or anticancer agent sensitivity mode (mode under which efficacy (sensitivity) of anticancer agents is judged) is executed (step S2). Specifically, two mode entry buttons are displayed on the display unit 79 of the personal computer 12. The operator clicks the entry button he/she needs to use. In this example, in the anticancer agent sensitivity mode, sensitivity of taxane-based anticancer agent is being judged. In addition to above-mentioned two modes, it may be configured that prognostic prediction/anticancer agents sensitivity mode are selected.

Subsequently, judgment of whether or not instruction for measurement start is being accepted is made (step S3). If Yes, it proceeds to step S4 and if No, it proceeds to step S8. Next, preparation of fluorescence detection sample (step S4) is carried out by sucking from the sample container set to the first reagent set unit 5 a sample and by executing a predetermined processing to the sample being sucked. The processing of this step includes preparation of expression level measurement sample and preparation of activity value measurement sample, which will be dealt with later, and these two processings are executed in parallel.

The chip set unit 1, in which measurement chip 121 (Reagent No. 3004) containing fluorescence detection sample is set, is moved from the position shown in FIG. 3 into the detection unit 4 (step S5), exciting light is radiated to each well of the measurement chip, and fluorescence emitted from a sample for fluorescence detection is detected (step S6).

Next, fluorescence intensity is obtained by the control unit 77 of the personal computer 12 and results of analysis derived from fluorescence intensity are output (step S7). Judgment is made whether or not instruction for determination apparatus shutdown is accepted (step S8) and if Yes, it proceeds to S9 and if No, it returns to step S1. Shutdown processing is made at the end and the power is turned OFF (step S9).

(4) Preparation Processing of Expression Level Measurement Sample

Figure 19:
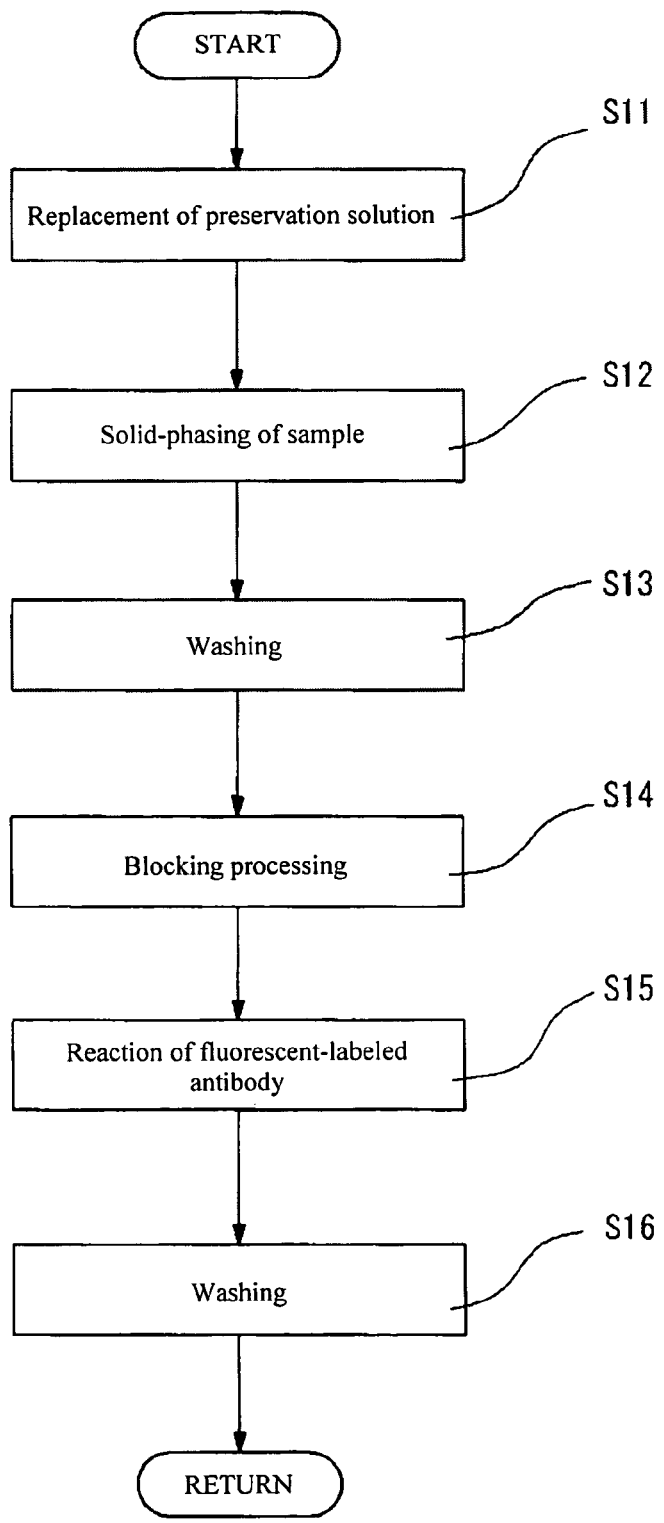
FIG. 19 is a drawing showing flow of preparation processing of a sample for measurement of expression level.

FIG. 19 shows flowchart of preparation of expression level measurement sample in step S4. First, preservation solution (TBS; 25 mM Tris, 150 mM NaCl, pH 7.4) accumulated in advance in each well of the measurement chip 121 (Reagent No. 3003) was drained and inside of each well was washed (step S11). Washing took place in such that washing solution (Reagent No. 3002) was filled from the above to each well via a pipette of the dispensing mechanism unit 3 and the washing solution being filled was sucked from lower part of the measurement chip by negative pressure via hydrophobic porous membrane. The same also applies to the following washing processes.

Next, a sample being prepared for expression level measurement was sucked from the sample container set to the first reagent set unit 5 using a pipette, the sample was filled into a prescribed well, and then the sample was sucked from lower part of the measurement chip 121 (Reagent No. 3004) by negative pressure. With these manipulations, proteins contained in the sample are held by hydrophobic bonding or the like with regard to hydrophobic porous membranes and are solid-phased (step S12). Next, inside of said predetermined well was washed with a similar manner as step S11. By these manipulations, constituents other than proteins were removed from the hydrophobic porous membranes of the measurement chip (step S13).

Following this, blocking solution (Reagent No. 1014) being set to the first reagent set unit 5 was sucked using a pipette and filled into a predetermined well, left for more than 15 min. (e.g., 30 min.), and blocking solution remained in the well was drained (step S114). By these manipulations, it is possible to prevent fluorescent labeled CDK1 antibody solution (Reagent No. 1001), fluorescent labeled CDK2 antibody solution (Reagent No. 1002), fluorescent labeled p21 antibody solution (Reagent No. 1003), and fluorescent labeled GAPDH antibody solution (Reagent No. 1004) to be filled subsequently from solid-phasing to hydrophobic porous membrane portion where proteins are not solid-phased. Next, the fluorescent labeled CDK1 antibody solution, the fluorescent labeled CDK2 antibody solution, the fluorescent labeled p21 antibody solution, the fluorescent labeled GAPDH antibody solution and background solution (Reagent No. 1013) were filled into two wells. After 20 to 30 min. when reaction between each of fluorescent-labeled antibody solution and proteins (CDK1, CDK2, p21 or GAPDH) solid-phased to the hydrophobic porous membrane was complete, each of fluorescent-labeled antibody solution being filled was drained (step S15). At the end, inside of the predetermined well was washed with a similar manner as step S13 (step S16).

As for twin simultaneous accessible container accommodating, in addition to blocking solution (Reagent No. 1014), before reaction buffer 1 (Reagent No. 2005), before reaction buffer 2 (Reagent No. 2006) and fluorescent enhanced reagent (Reagent No. 2009), two liquid reservation parts are provided having width that allows simultaneous solution suction by two pipettes of the dispensing mechanism unit 3.

(5) Preparation Processing of Activity Value Measurement Sample

Figure 20:
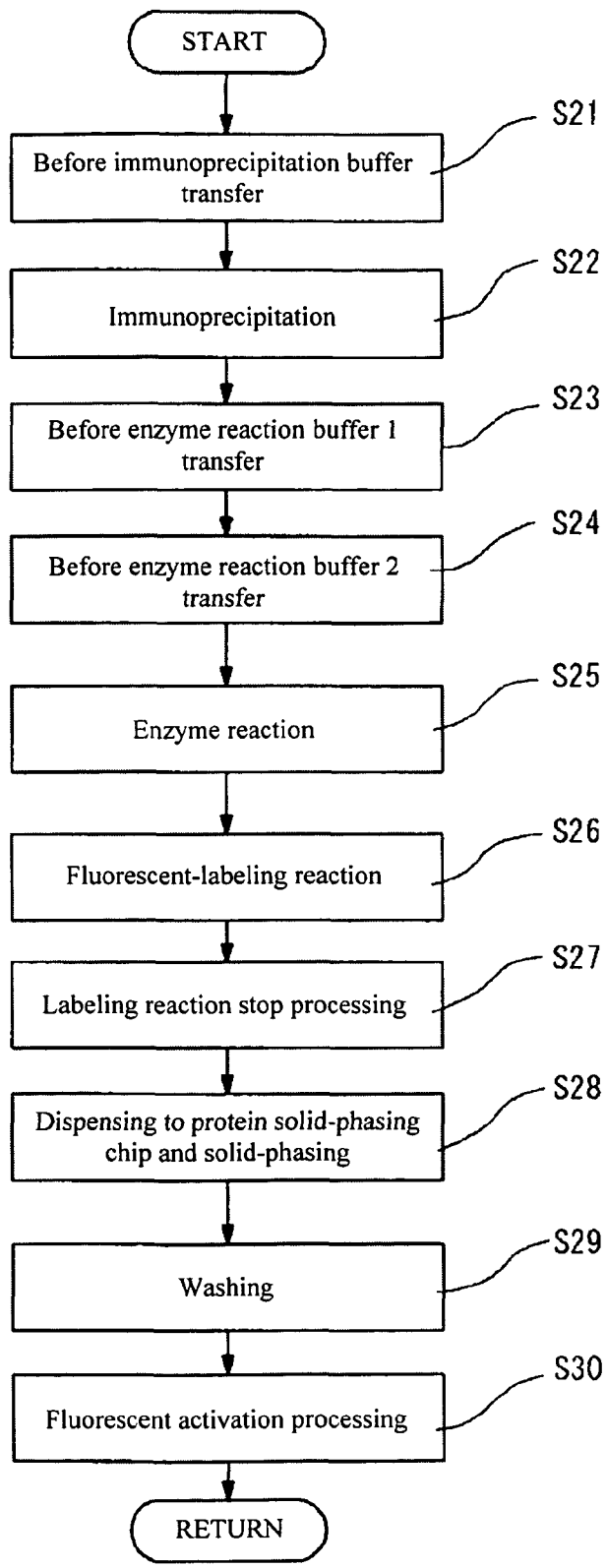
FIG. 20 is a drawing showing flow of preparation processing of a sample for measurement of activity.

FIG. 20 shows flowchart of preparation processing of activity value measurement sample in step S4. In this preparation processing of activity value measurement sample, as the activity measurement unit 2 shown in FIG. 3, such one having four sample preparation units 211 at this side and having four sample preparation units 211 also in the back side in the drawing was used. In this activity measurement unit 2, each of sample preparation units 211 is referred to, from left in the back side in the drawing, to first sample preparation unit (Ac1), second sample preparation unit (Ac2), third sample preparation unit (Ac3) and fourth sample preparation unit (Ac4), and from left at this side in the drawing, fifth sample preparation unit (Ac5), sixth sample preparation unit (Ac6), seventh sample preparation unit (Ac7) and eighth sample preparation unit (Ac8).

Figure 21:
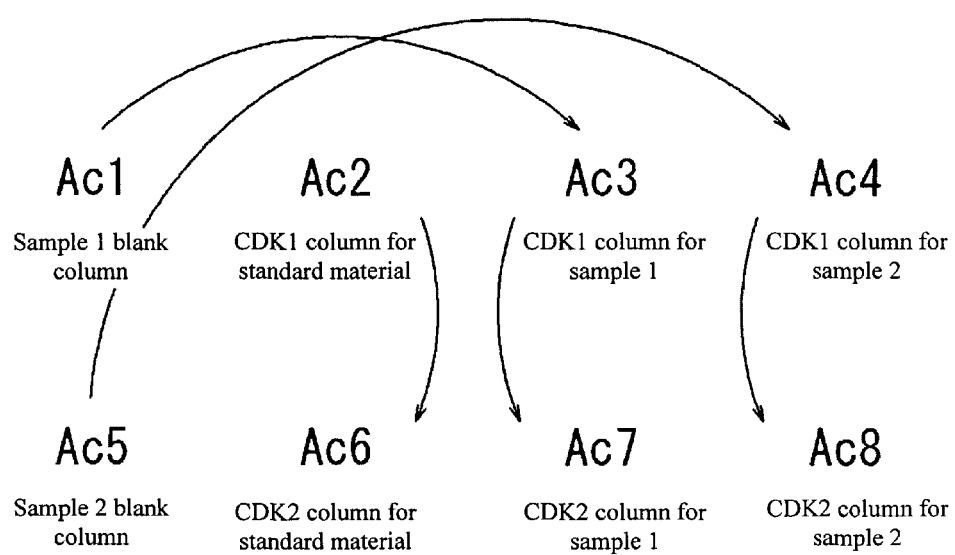
FIG. 21 is a drawing explaining an example of utilizing a sample for measurement of activity.

First, a total of eight columns—three CDK1 columns (Reagent No. 2001), three CDK2 columns (Reagent No. 2002) and two blank columns (Reagent No. 2003)—(hereinafter, abbreviated as each column in some cases) were set to the first to eighth sample preparation units (Ac1 to Ac8) as shown in FIG. 21 and for each of the first to eighth sample preparation units (Ac1 to Ac8), immunoprecipitation buffer (Reagent No. 2004) was filled to the liquid receiving part 222 using a pipette of the dispensing mechanism unit 3. Then the buffer is transferred to each of eight columns for each of the first to eighth sample preparation units (Ac1 to Ac8), while the syringe pump 214 and electromagnetic valves 224, 225 are operating as mentioned previously. The immunoprecipitation buffer in each of all columns was discarded by sucking using a pipette of the dispensing mechanism unit 3 (step S21).

Next, immunoprecipitation (reaction between antibody and CDK) was caused (step S22). FIG. 21 shows the order of liquid transfer of samples. First, from one of sample containers being set to the first reagent set unit 5, sample 1 for activity measurement was sucked by one pipette and sample 2 for activity measurement was sucked by the other pipette of the dispensing mechanism unit 3.

The sample 1 for activity measurement being sucked from the sample container was filled into the liquid receiving part 222 of the first sample preparation unit (Ac1) and from this, was then transferred to the blank column (Reagent No. 2003) being set to the first sample preparation unit (Ac1), while the syringe pump 214 and electromagnetic valves 224, 225 were operating. On this occasion, by moving the piston 218 upwardly/downwardly 1.5 reciprocations (exhaust-suction-exhaust), the sample 1 was moved 1.5 reciprocations in the carrier consisted of monolith silica gel of the blank column.

In the meantime, the sample 2 for activity measurement being sucked from the sample container was first filled to the liquid receiving part 222 of the fifth sample preparation unit (Ac5) and from this, in a similar manner as mentioned above, was then transferred to the blank column (Reagent No. 2003) being set to the fifth sample preparation unit (Ac5). Neither antibody of CDK1 nor antibody of CDK2 was immobilized to the monolith silica gel carrier of the blank column of the first sample preparation unit (Ac1) and the fifth sample preparation unit (Ac5). Therefore, CDK1 and CDK2 are not solid-phased in the first sample preparation unit (Ac1) and the fifth sample preparation unit (Ac5), while sample 1 containing CDK1 and CDK2 is accumulated in the blank column being set to the first sample preparation unit (Ac1), and sample 2 containing CDK1 and CDK2 is accumulated in the blank column being set to the fifth sample preparation unit (Ac5).

Next, sample 1 accumulated in the blank column being set to the first sample preparation unit (Ac1) is sucked by a pipette of the dispensing mechanism unit 3, filled to the liquid sample receiving part 222 of the third sample preparation unit (Ac3) and from this, in a similar manner as mentioned above, is then transferred to CDK1 column (Reagent No. 2001) being set to the third sample preparation unit (Ac3).

In the meantime, sample 2 accumulated in the blank column being set to the fifth sample preparation unit (Ac5) is sucked by a pipette of the dispensing mechanism unit 3, filled to the liquid sample receiving part 222 of the fourth sample preparation unit (Ac4) and from this, in a similar manner as mentioned above, is then transferred to CDK1 column (Reagent No. 2001) being set to the fourth sample preparation unit (Ac4). Antibody of CDK1 is immobilized to the monolith silica gel carrier of CDK1 column being set to the third sample preparation unit (Ac3) and the fourth sample preparation unit (Ac4). Therefore, in the third sample preparation unit (Ac3) and the fourth sample preparation unit (Ac4), although CDK1 is solid-phased, CDK2 is not solid-phased, and sample 1 not containing CDK1 but containing CDK2 is accumulated in the CDK1 column being set to the third sample preparation unit (Ac3), and sample 2 not containing CDK1 but containing CDK2 is accumulated in the CDK1 column being set to the fourth sample preparation unit (Ac4).

Next, sample 1 accumulated in the CDK1 column (Reagent No. 2001) being set to the third sample preparation unit (Ac3) is sucked by a pipette of the dispensing mechanism unit 3, filled to the liquid sample receiving part 222 of the seventh sample preparation unit (Ac7) and from this, in a similar manner as mentioned above, is then transferred to CDK2 column (Reagent No. 2002) being set to the seventh sample preparation unit (Ac7).

In the meantime, sample 2 accumulated in the CDK1 column (Reagent No. 2001) being set to the fourth sample preparation unit (Ac4) is sucked by a pipette of the dispensing mechanism unit 3, filled to the liquid sample receiving part 222 of the eighth sample preparation unit (Ac8) and from this, in a similar manner as mentioned above, is then transferred to CDK2 column (Reagent No. 2002) being set to the eighth sample preparation unit (Ac8). Antibody of CDK2 is immobilized to the monolith silica gel carrier of CDK2 column being set to the seventh sample preparation unit (Ac7) and the eighth sample preparation unit (Ac8). Therefore, CDK2 is solid-phased in the seventh sample preparation unit (Ac7) and the eighth sample preparation unit (Ac8) and therefore, sample 1 containing neither CDK1 nor CDK2 is accumulated in the CDK2 column being set to the seventh sample preparation unit (Ac7), and sample 2 containing neither CDK1 nor CDK2 is accumulated in the CDK2 column being set to the eighth sample preparation unit (Ac8). Sample 1 and sample 2 accumulated in the CDK2 column being set to the seventh sample preparation unit (Ac7) and the eighth sample preparation unit (Ac8) are respectively sucked by a pipette of the dispensing mechanism unit 3, and are discarded in the waste fluid bath 7.

Meanwhile, the first sample preparation unit (Ac1) and the fifth sample preparation unit (Ac5) are used for activity measurement of background, the third sample preparation unit (Ac3) and the fourth sample preparation unit (Ac4) are used for activity measurement of CDK1, and the seventh sample preparation unit (Ac7) and the eighth sample preparation unit (Ac8) are used for activity measurement of CDK2.

As such, by filling a sample remained in a column into other column, background activity measurement, CDK1 activity measurement and CDK2 activity measurement are made possible with a small amount of sample.

In order to prepare a calibration curve of the activity, calibrator solution for activity (Reagent No. 2011) was measured using same procedures as mentioned above.

Subsequently, in order to remove unnecessary constituents in the sample by washing, before reaction buffer 1 (Reagent No. 2005) was transferred to each column (step S23). After that, since before reaction buffer 1 (Reagent No. 2005) has an influence on enzyme reaction executed in step S25, with primary purpose of providing conditions for such enzyme reaction, before reaction buffer 2 (Reagent No. 2006) was transferred to each column to wash away constituents of before reaction buffer 1 (Reagent No. 2005).

Subsequently, substrate solution (Reagent No. 2007) is filled in each column and the piston 219 was reciprocated 5.5 times (step S25). The liquid being pushed out from lower part of each column is accumulated directly in each column. By this step, phosphate group is introduced into Histon H1 contained in the substrate solution, while CDK1 or CDK2 acts as the enzyme. Since the amount of the phosphate group is governed by the intensity of action (i.e., activity value) of CDK1 or CDK2 as the enzyme, it is possible to obtain the activity value of CDK1 or CDK2 by measuring the amount of said phosphate group. Meanwhile, background activity value obtained by using the first sample preparation unit (Ac1) and the fifth sample preparation unit (Ac5) shown in FIG. 21 was used for the sake of background correction which will be dealt with later.

Next, fluorescent labeled solution (Reagent No. 2008) was dispensed directly to each column inside from the above of each column using a pipette and a fluorescent label was bound to the phosphate group being introduced into Histon H1 (step S26). On this occasion, liquid in each column was stirred by repeating dispensing and suction of liquid in each column using a pipette for a predetermined time. After a predetermined time from initiation of step S26 (e.g., 20 min.), reaction stopper (Reagent No. 2010) was dispensed directly to each column with a similar manner as observed for the fluorescence-labeling reagent. Then liquid in each column was stirred (step S27) by repeating dispensing and suction of liquid in each column for a predetermined time likewise step S26. By these manipulations, binding of the fluorescent label was stopped.

Subsequently, liquid in a total of six columns of first sample preparation unit (Ac1), third sample preparation unit (Ac3), fourth sample preparation unit (Ac4), fifth sample preparation unit (Ac5), seventh sample preparation unit (Ac7) and eighth sample preparation unit (Ac8) was dispensed respectively into six wells of the measurement chip 121 (Reagent No. 3004), and then the measurement chip 121 was sucked from lower part (step S28). By these manipulations, Histon H1 having phosphate group to which fluorescent label is bound is solid-phased to porous membrane of the measurement chip 121. Then, wells were washed with washing solution (Reagent No. 3002) (step S29) likewise step S11 used in the preparation of said development level measurement sample. At the end, in order to activate fluorescence, fluorescent enhanced reagent (Reagent No. 2009) was dispensed to wells and then drained. This operation was repeated six times (step S30).

(6) Analytical Processing

Figure 22:
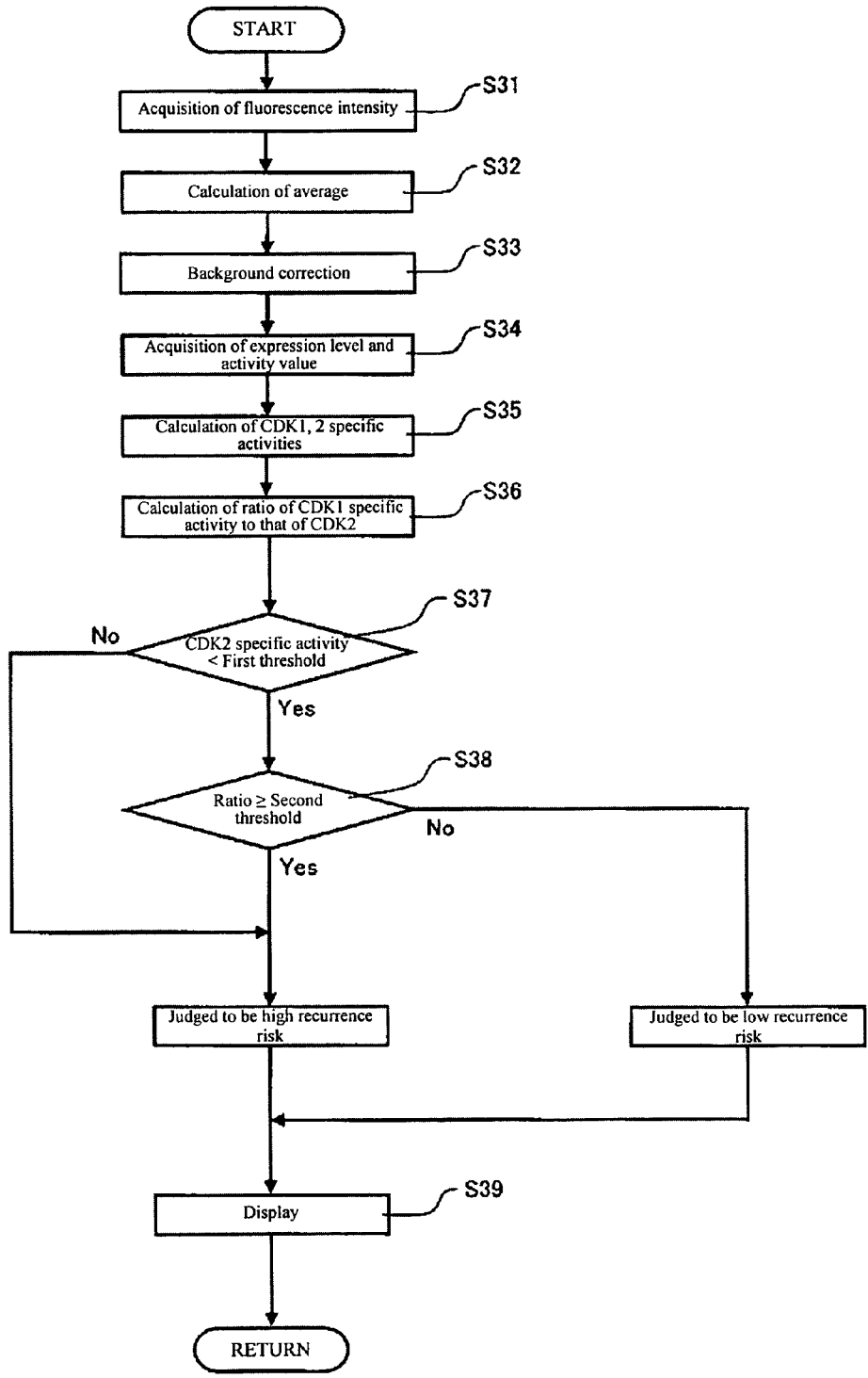
FIG. 22 is a drawing showing entire flow of one example of analytical processing by the determination apparatus.

As shown in FIG. 22, analysis is made using fluorescence intensity obtained by the detection unit and results of the analysis are outputted. The control unit 77 acquires, from light receiving system of the detection unit 4 via the electronic circuit board 10, each two fluorescence intensity for each of expression of CDK1, activity of CDK1, expression of CDK2, activity of CDK2, expression of p21, expression of background, and activity of background (step S31).

Subsequently, the control unit 77 calculates average of the fluorescence intensity obtained each two for every item (step S32). Next, background correction is carried out for CDK1 expression, CDK2 expression and p21 expression by subtracting background expression (average) from fluorescence intensity (average) of expression of CDK1 and subtracting background expression (average) from fluorescence intensity (average) of expression of CDK2. Background correction is also carried out similarly for CDK1 activity, CDK2 activity and p21 activity (step S33).

Subsequently, expression level and activity are acquired using a calibration curve for each of items (step S34). Meanwhile, this calibration curve is a data used for converting fluorescence intensity to expression level or activity value. As for preparation of a calibration curve, first, calibration curve of expression level was prepared using results of expression level measurements of previously mentioned CDK1 antigen solution 1 (Reagent No. 1005), CDK1 antigen solution 2 (Reagent No. 1006), CDK2 antigen solution 1 (Reagent No. 1007), CDK2 antigen solution 2 (Reagent No. 1008), p21 antigen solution 1 (Reagent No. 1009), p21 antigen solution 2 (Reagent No. 1010), GAPDH antigen solution 1 (Reagent No. 1011) and GAPDH antigen solution 2 (Reagent No. 1012). Further, calibration curve of activity was prepared using results of activity measurements of previously mentioned calibrator solution for activity (Reagent No. 2011). These calibration curves for expression level and activity value are stored in RAM91c of the control unit 77. Specific activity of CDK1 and specific activity of CDK2 are then calculated according to the following equations (step S35):

Specific activity of CDK1=Activity value of CDK1/Expression level of CDK1

Specific activity of CDK2=Activity value of CDK2/Expression level of CDK2

Besides, ratio of CDK1 specific activity to CDK2 specific activity is calculated according to the following equation (step S36):

Ratio of CDK1 specific activity to CDK2 specific activity=CDK2 specific activity/CDK1 specific activity Here, first, whether or not CDK2 specific activity is more than a first threshold (step S37) is judged, and when CDK2 specific activity is more than the first threshold, it is determined that recurrence risk of cancer is high. When CDK2 specific activity is less than the first threshold, judgment is made whether or not ratio of CDK1 specific activity to CDK2 specific activity is more than a second threshold (step S38), and when the ratio is more than the second threshold, it is determined that recurrence risk of cancer is high, and when the ratio is less than the second threshold, it is determined that recurrence risk of cancer is low. CDK1 expression level, CDK1 activity value, CDK1 specific activity, CDK2 expression level, CDK2 activity value, CDK2 specific activity and ratio of CDK1 specific activity to CDK2 specific activity, which are used as the grounds for determining the degree of recurrence risk, are displayed and at the same time, result of determination of recurrence risk is displayed (step S39).

Hereinafter, explanation will be given referring to a concrete example where expression level and activity value of breast cancer tissues were measured actually using the present reagent kit and recurrence risk was determined. Determination of recurrence risk was performed using above-mentioned method for sample tissues taken from four breast cancer patients W, X, Y and Z. Results of determination by the pathologist (TMN classification, status of metastasis to lymph node, size of cancer tissue, presence or absence of recurrence in five postoperative years, site of recurrence) for sample tissues from four breast cancer patients are shown in Table 8. Four patients had early stage cancer (LN is a) and sample tissues from frozen storage were used.

In the table, "LN" means status of metastasis to lymph node at surgery, "a" means metastasis is not recognized with regional lymph node, "b" means metastasis is recognized at 1 to 3 sites with regional lymph node, and "c" means metastasis is recognized at more than 4 sites with regional lymph node. "T" means size of primary focus at surgery and one with tumor diameter smaller than 2 cm is represented by "a", tumor diameter in 2 cm to 5 cm by "b", and tumor diameter larger than 5 cm is represented by "c".

For sample tissues taken from four breast cancer patients, CDK1 specific activity and CDK2 specific activity were measured and recurrence risk of sample tissues was determined using said reagent kit and tissue characteristic determination apparatus. Ratio of CDK1 specific activity to CDK2 specific activity of sample tissues taken from breast cancer patients W, X, Y and Z are shown in Table 8, respectively. First, a first threshold was set to 10000 in advance and it was compared with CDK2 specific activity. The sample tissue from breast cancer patient X whose ratio was the first threshold (10000) or higher was determined to have higher risks of cancer. Next, a second threshold was set to 46 in advance and it was compared with the ratio of CDK1 specific activity to CDK2 specific activity. The sample tissue from breast cancer patient Z whose ratio was more than the second threshold (46) was determined to have higher risks of cancer recurrence, while sample tissues from breast cancer patients W and Y whose ratio is less than the second threshold were determined to have lower risks of cancer recurrence. Results are shown in Table 8.

TABLE 8

| Patient | TMN | LN | T | CDK2 specific activity/CDK1 specific activity | Recurrence risk | Recurrence | Recurrence part |
|---------|-----|-----|-----|----|----|----|----|
| W | stage I | a | a | 28.86 | Low | No | — |
| X | stage I | a | a | CDK2 specific activity ≧10000 | High | Yes | Lung |
| Y | stage IIA | a | b | 2.33 | Low | No | — |
| Z | stage IIA | a | b | 148.68 | High | Yes | Skin |

As shown in Table 8, even with early stage breast cancers malignancy of which is believed to be not so high, results of the measurement using said reagent kit and tissue characteristic determination apparatus indicated that recurrence risk of patients X and Z was high and in fact they has a relapse within five years after surgery. In the meantime, patients W and Y who were determined to have lower recurrence risks did not experience a relapse.

Figure 23:
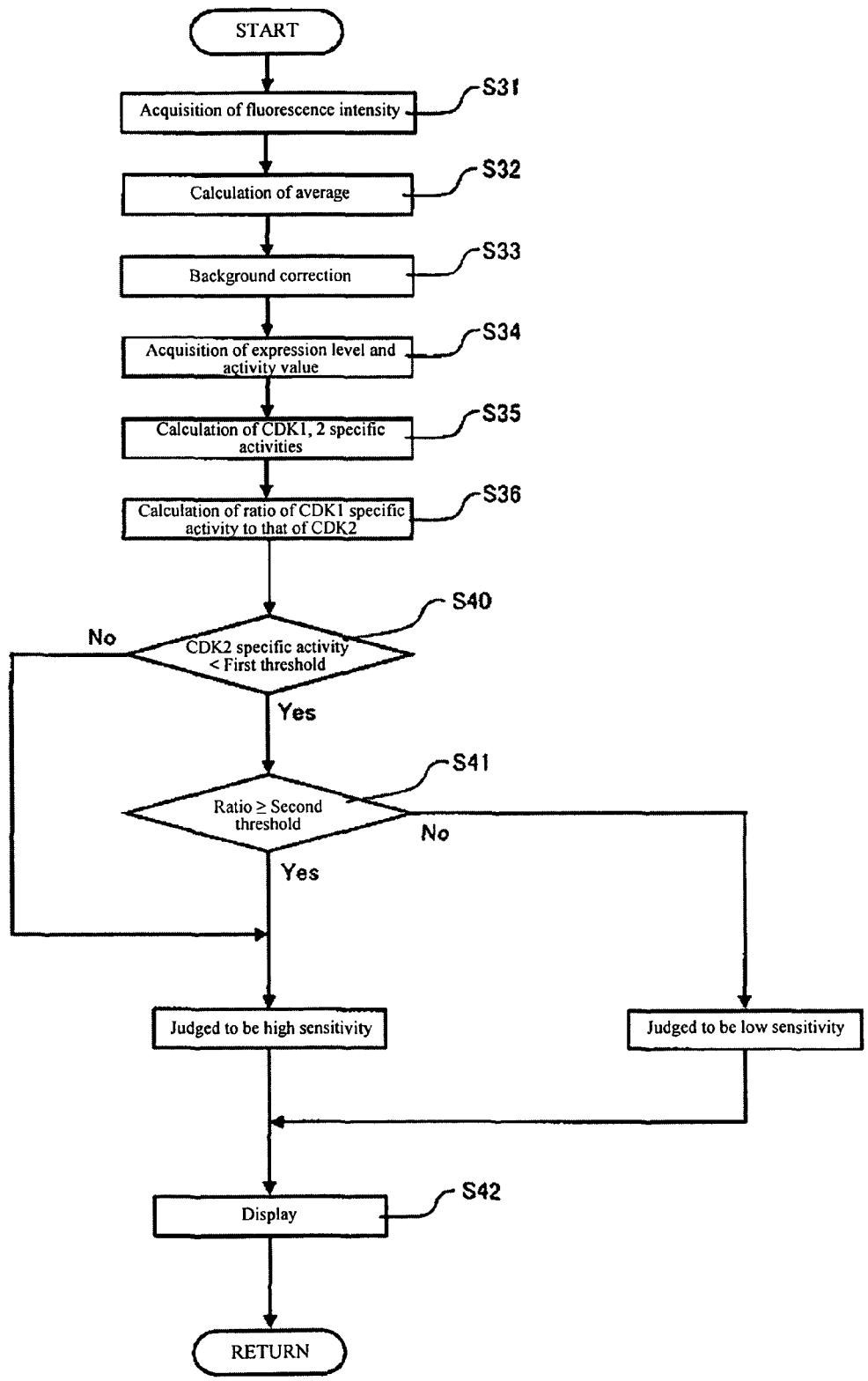
FIG. 23 is a drawing showing entire flow of another example of analytical processing by the determination apparatus.

FIG. 23 is a drawing showing flowchart of other embodiments of analytical processing shown in FIG. 22. In this embodiment, in step S40, sensitivity of taxane-based anticancer agent was determined. In the analytical processing shown in this embodiment, from step S31 to step S36 are identical with the analytical processing shown in FIG. 21.

Here, judgment is made whether or not said CDK2 specific activity is more than the first threshold (step S40), and when CDK2 specific activity is more than the first threshold, it is determined that sensitivity to anticancer agent is high, i.e., the anticancer agent is effective. When CDK2 specific activity is less than the first threshold, whether or not ratio of said CDK1 specific activity to CDK2 specific activity is more than a third threshold (step S41), and when the ratio is more than the third threshold, it is determined that sensitivity to anticancer agent is high, and when the ratio is less than the third threshold, it is determined that sensitivity to anticancer agent is low. CDK1 expression level, CDK1 activity value, CDK1 specific activity, CDK2 expression level, CDK2 activity value, CDK2 specific activity and ratio of CDK1 specific activity to CDK2 specific activity, which are used as the grounds for determining each of above mentioned determinations are displayed and at the same time, result of determination of the sensitivity of anticancer agents are displayed (step S42).

Hereinafter, a concrete example of measuring expression level and activity of breast cancer tissues using the present reagent kit actually and determining sensitivity for above-mentioned taxane-based anticancer agent will be explained. For sample tissues taken from breast cancer patients O, P, Q, sensitivity to taxane-based anticancer agent was determined using above-mentioned method. Results of determination by the pathologist (TMN classification, status of metastasis to lymph node, size of cancer tissue, effects by anticancer agent treatment) for sample tissues from three breast cancer patients are shown in Table 9. Three patients had progressive cancer (LN is c or b) and sample tissues were taken for biopsy purpose.

Using the reagent kit and tissue characteristic determination apparatus, for sample tissues derived from three breast cancer patients O, P, Q who have not undergone anticancer agent treatment, CDK1 specific activity and CDK2 specific activity were measured to determine the sensitivity to taxane-based anticancer agent. Ratio of CDK specific activity to CDK2 specific activity of sample tissues taken from breast cancer patients O, P, Q are shown in Table 9, respectively. Here, a first threshold was set to 10000 in advance and was compared with CDK2 specific activity likewise those shown in FIG. 21. Sample tissues from breast cancer patients P and Q who had the ratio more than the first threshold (10000) showed higher sensitivity to the anticancer agent, namely, it was determined that the anticancer agent is effective. Then, a third threshold was set to 48 in advance and was compared with ratio of CDK1 specific activity to CDK2 specific activity 2. For sample tissue from breast cancer patient O who had the ratio more than the third threshold (48), it was also determined that sensitivity to anticancer agent is high. Results are shown in Table 9. "PR" (partial response) shown in the table means that reduction was attained in more than 50% of total of measurable lesions and new lesion did not appear.

As shown in Table 9, in sample tissues determined to have high sensitivity to anticancer agents, remarkable effects of anticancer agent treatment were recognized.

(7) Example of Utilization of Determination Results

Figure 24:
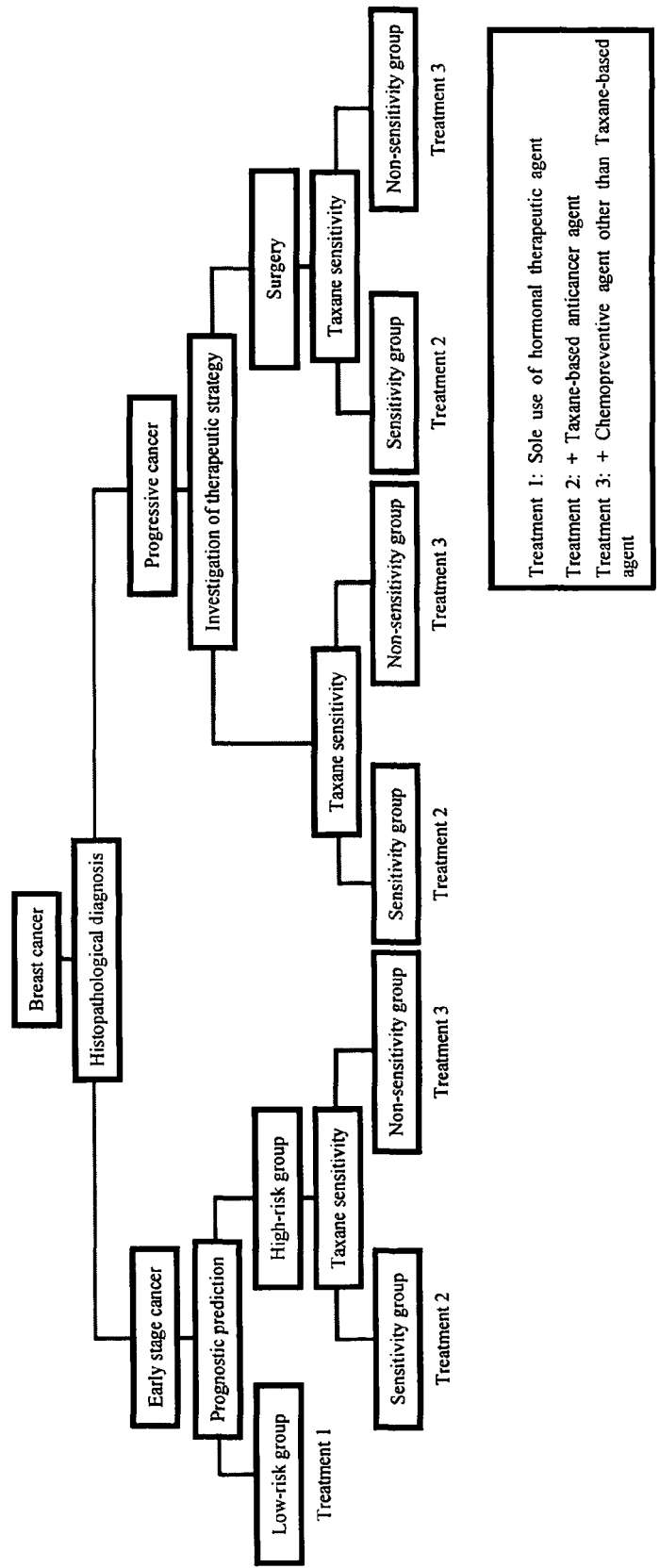
FIG. 24 is a drawing showing an example of utilizing determination result obtained by measurements.

FIG. 24 shows how medical doctors utilize determination results shown in step S39 shown in FIG. 22 and step S42 shown in FIG. 23.

For a particular patient, possibility of breast cancer is confirmed by diagnostic imaging and presence of a cancer is established by histopathological diagnosis by biopsy or by cytological diagnosis. When the patient is diagnosed as having early stage cancer by the result of histopathological diagnosis, cancer tissues are removed and determination of a characteristic is made using the determination apparatus A for tissues removed. In a case it has been revealed that the cancer belongs to low-risk group (determination result displayed by determination apparatus A is "recurrence risk is low") as the result of determination of tissue characteristic by determination apparatus A, treatment 1 (sole use of hormonal therapeutic agent) is selected by the doctor. When revealed that the cancer belongs to high-risk group (determination result displayed by determination apparatus A is "recurrence risk is high"), judgment of sensitivity to taxane-based anticancer agents is performed. When it has been revealed that the cancer longs to taxane sensitivity group, use of taxane-based anticancer agent is effective, (determination result displayed by determination apparatus A is "sensitivity to anticancer agent is high"), treatment 2 (concomitant administration of hormonal therapeutic agent and taxane-based anticancer agent) is selected. In the meantime, when determination result displayed by determination apparatus A is "sensitivity to anticancer agent is low", since it is premature to conclude that taxane is effective, treatment 2 (concomitant administration of hormonal therapeutic agent and taxane-based anticancer agent) or treatment 3 (concomitant administration of hormonal therapeutic agent and chemopreventive agent other than taxane) is selected by doctor's judgment.

In a case the patient is diagnosed as having progressive cancer by histopathological diagnosis, discussion is held between the doctor and the patient whether or not preoperative chemotherapy (treatment by chemopreventive agent before extirpative surgery) be used considering various factors including life style of the patient, desire for breast conservation, medical expenses or the like. When preoperative chemotherapy is performed, anticancer agent sensitivity judgment by the determination apparatus A is performed for biopsy samples being immersed in the anticancer agent (taxane) for 24 hours. In a case determination result displayed by the determination apparatus A is "anticancer agent sensitivity is high", treatment 2 (concomitant administration of hormonal therapeutic agent and taxane-based anticancer agent) is selected. When determination result displayed by the deter-

TABLE 9

| Patient | TMN | LN | T | CDK2 specific activity/CDK1 specific activity | Anticancer agent sensitivity | Anticancer agent therapeutic effects |
|---------|-----------|---|---|-----------------------------------------------|------------------------------|--------------------------------------|
| O | stage IIIB | b | c | 302.56 | High | PR |
| P | stage IIIB | c | b | CDK2 specific activity ≧10000 | High | PR |
| Q | stage IIIB | b | c | CDK2 specific activity ≧10000 | High | PR | mination apparatus A is "anticancer agent sensitivity is low", since efficacy of taxane is not definite, either treatment 2 (concomitant administration of hormonal therapeutic agent and taxane-based anticancer agent) or treatment 3 (concomitant administration of hormonal therapeutic agent and chemopreventive agent other than taxane) is selected by doctor's decision. After cancer tissue is reduced by the anticancer agent by performing preoperative chemotherapy appropriately using these determinations results as the guidance, it can be excised.

When no chemotherapy is employed, extirpative surgery is performed and judgment of anticancer agent sensitivity by the determination apparatus A is carried out for cancer tissues removed. When determination result displayed by the determination apparatus A is "anticancer agent sensitivity is high", treatment 2 (concomitant administration of hormonal therapeutic agent and taxane-based anticancer agent) is selected. In a case determination result displayed by the determination apparatus A is "anticancer agent sensitivity is low", since efficacy of taxane is not definite, either treatment 2 (concomitant administration of hormonal therapeutic agent and taxane-based anticancer agent) or treatment 3 (concomitant administration of hormonal therapeutic agent and chemopreventive agent other than taxane) is selected by doctor's decision.

Figure 25:
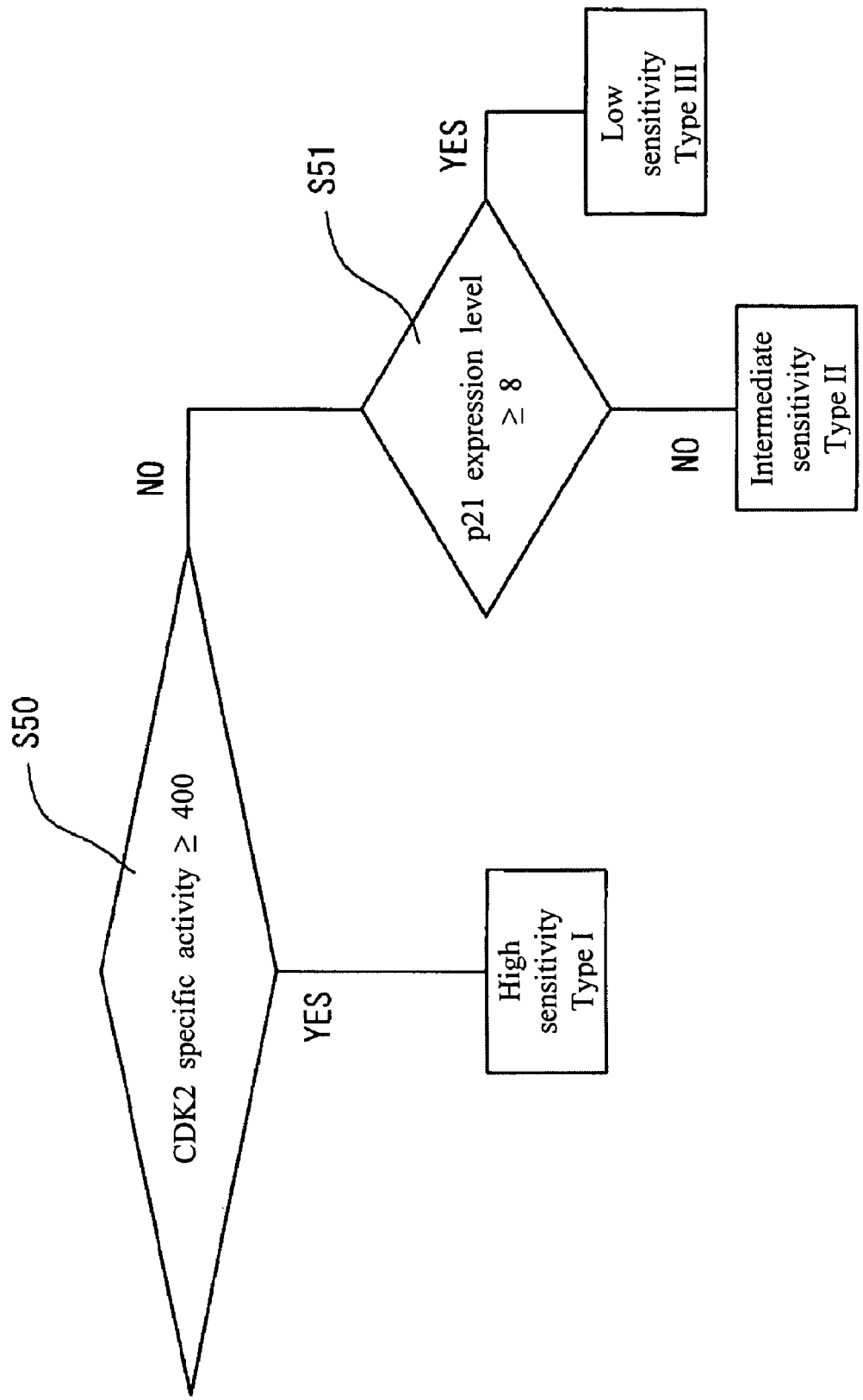
FIG. 25 is a drawing showing another flow relating to analysis of sensitivity.

FIG. 25 shows another flowchart relating to sensitivity analysis. In this flowchart, sensitivity of taxane-based anticancer agent is also determined in such that comparison between CDK2 specific activity and threshold "400" is made (step S50) and when CDK2 specific activity is more than 400, it is judged to be higher sensitivity type I, and when CDK2 specific activity is less than 400, comparison between expression level of p21 and threshold "8" is made (step S51). When expression level of p21 is more than 8, it is judged to be lower sensitivity type III, and when expression level of p21 is less than 8, it is judged to be intermediate sensitivity type II. In this embodiment, CDK2 specific activity and each threshold of expression level of p21 can be set based on patient data or the like accumulated in advance.

Figure 26:
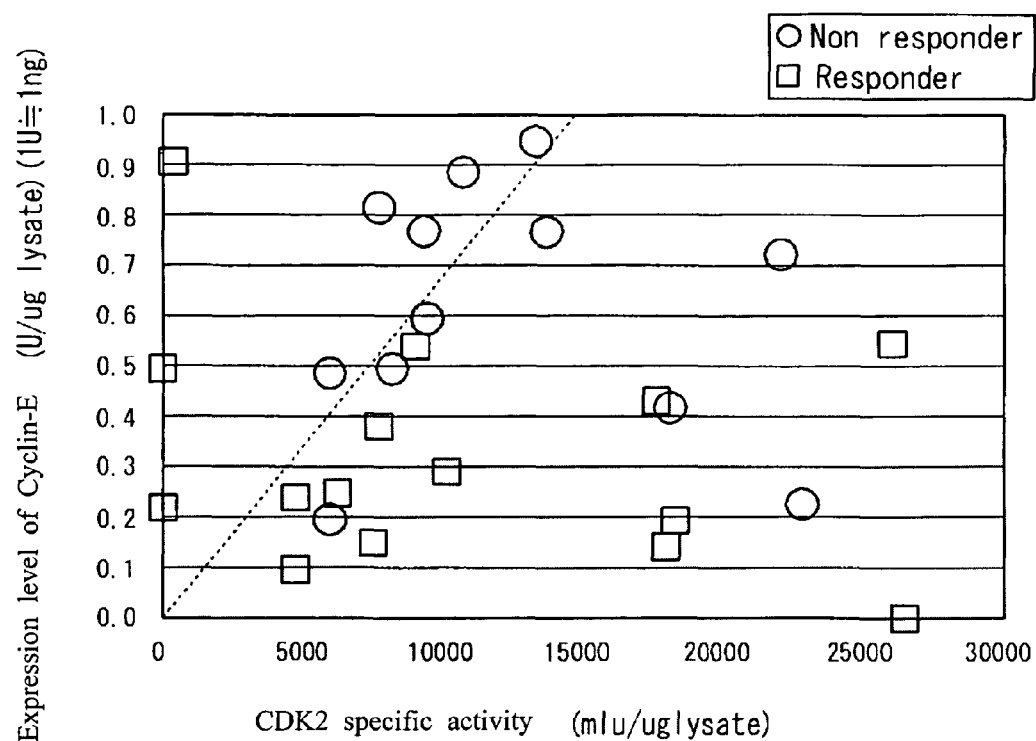
FIG. 26 is a drawing showing still another determination result relating to analysis of sensitivity.

FIG. 26 shows other determination results relating to sensitivity analysis. In FIG. 26, sensitivity of CE (anticancer agent) is determined based on expression level of cyclin E and specific activity value of CDK2. Specifically, sensitivity of CE is determined by comparing ratio of CDK2 specific activity to cyclin E expression level with predetermined threshold. In the meantime, expression level of cyclin E can be measured with a similar manner as expression level of CDK1 by changing reagents appropriately.

Figure 27:
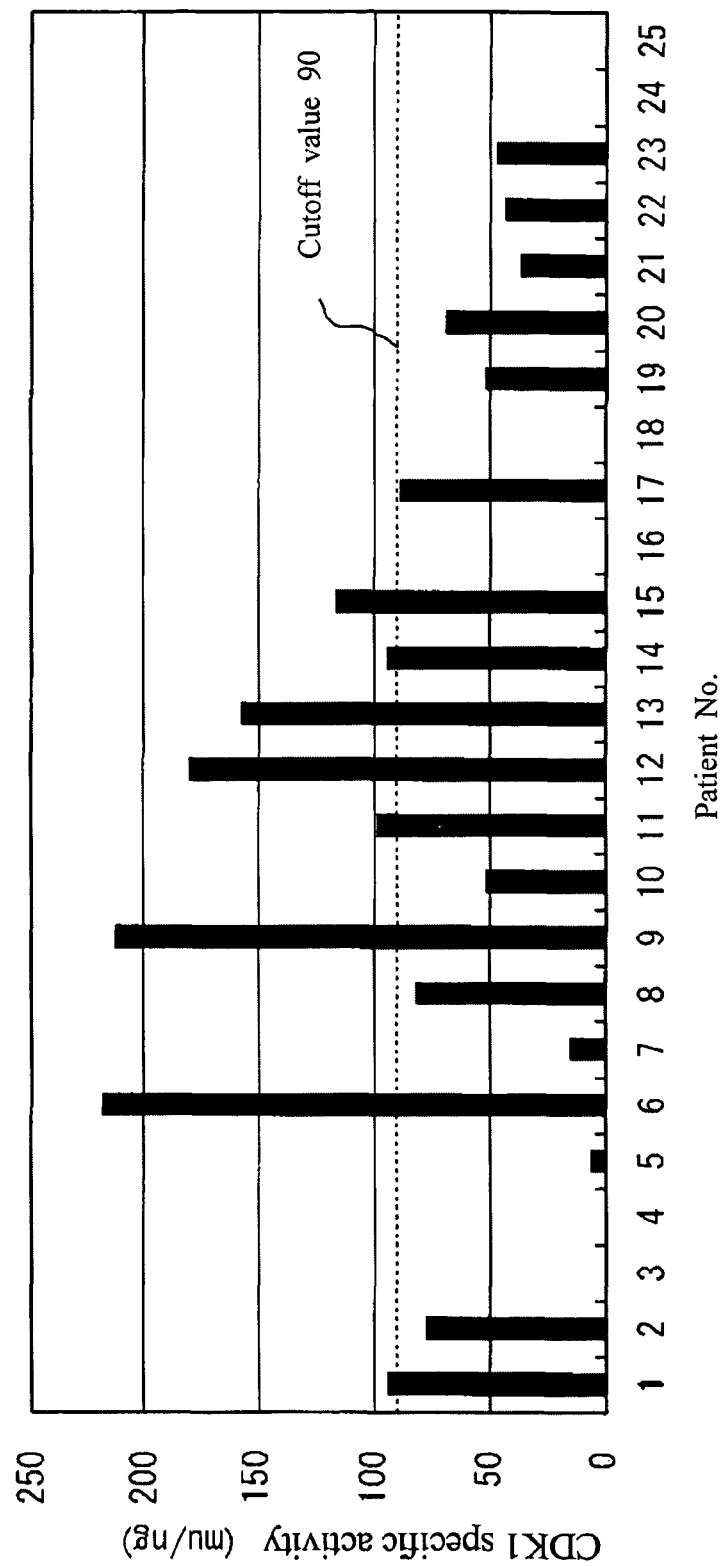
FIG. 27 is a drawing showing still another determination result relating to analysis of sensitivity.

FIG. 27 shows other determination results relating to sensitivity analysis. In FIG. 27, sensitivity of CMF (anticancer agent) is determined by comparison between specific activity value of CDK1 and a predetermined threshold. As far as the results shown are concerned, recurrence of cancer was not recognized with patients No. 1 to 16 due to treatment by CMF after extirpative surgery, while with patients No. 17 to 25, the cancer recurred notwithstanding treatment by CMF. In this case, if "90" is set as the threshold, eight cases with CDK1 specific activity more than 90 (No. 1, 6, 9, 11 to 15) are considered to be non-recurring cases and therefore, it is understood that a threshold of 90 is appropriate. For determination, tissues under frozen storage after removal were used.

Figure 28:
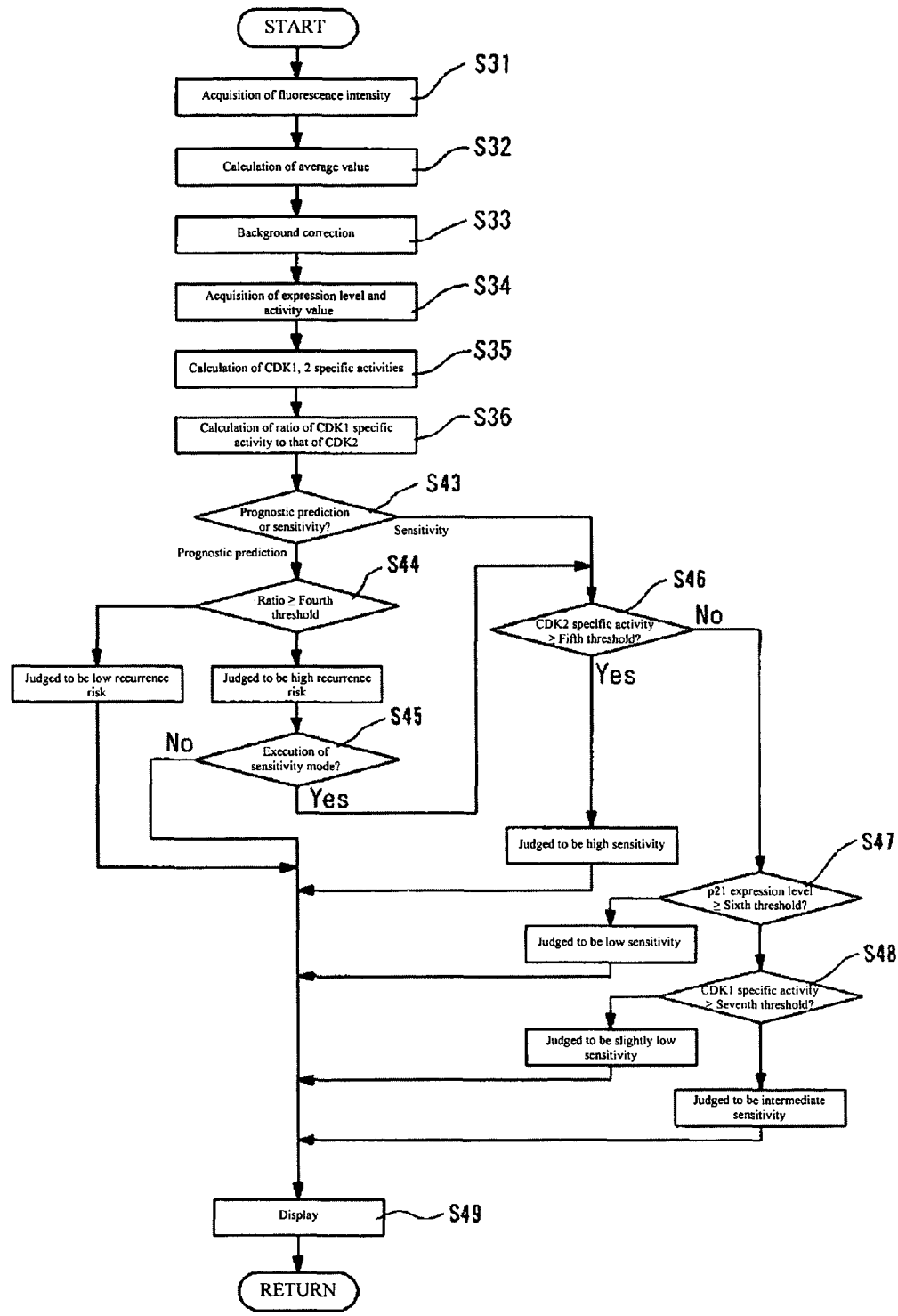
FIG. 28 is a drawing showing entire flow of another example of analytical processing by the determination apparatus.

FIG. 28 is a drawing showing still another flowchart of analytical processing shown in FIG. 22. In the analytical processing shown in this embodiment, from step S31 to step S36 are identical with the analytical processing shown in FIG. 22. In the analytical processing shown in this example, judgment is made in step S43 whether the mode selected in step S2 is prognostic prediction mode or sensitivity mode, and if prognostic prediction mode, judgment is made whether or not ratio of said CDK1 specific activity to CDK2 specific activity is more than a fourth threshold (step S44) and if sensitivity mode, judgment is made whether or not CDK2 specific activity is more than a fifth threshold (step S46). When, in step S44, ratio of CDK1 specific activity to CDK2 specific activity is more than the fourth threshold, it is judged to be higher recurrence risk and when ratio of CDK1 specific activity to CDK2 specific activity is less than the fourth threshold, it is judged to be lower recurrence risk. In a case it is judged to be higher recurrence risk, processing to make judgment whether or not sensitivity mode be executed is executed (step S45). Specifically, buttons are displayed on the display unit 79 of the personal computer 12 for selection of execution of sensitivity mode or display of only determination result of recurrence risk, and processing for accepting entry by the operator is executed. In step S45, when it is judged sensitivity mode is to be executed, the processing proceeds to step S46, and when it is judged sensitivity mode is to not be executed (only determination result of recurrence risk is displayed), the processing proceeds to step 49. When, in step S46, CDK2 specific activity is more than the fifth threshold, it is judged that sensitivity is high, namely, the anticancer agent is effective, while when CDK2 specific activity is less than the fifth threshold, comparison between p21 expression level and a sixth threshold is carried out (step S47).

When p21 expression level is less than the sixth threshold, it is judged that sensitivity is low, and when p21 expression level is more than the sixth threshold, comparison between CDK1 specific activity and a seventh threshold is carried out (step S48). When CDK1 specific activity is less than the seventh threshold, it is judged that sensitivity is slightly low, and when CDK1 specific activity is more than the seventh threshold, it is judged that sensitivity is at intermediate level.

CDK1 expression level, activity value specific activity, CDK2 expression level, activity value specific activity, ratio of CDK1 specific activity to CDK2 specific activity, and p21 activity level which are used for grounds for each of above-mentioned judgments are displayed and at the same time, judgment result of recurrence risk and of sensitivity are displayed depending on the mode selected (step S49).

As for fourth to seventh threshold, those described in International Application No. PCT/JP2005/009847 (WO 2005/116241) and those described in Japanese Patent Application No. 2005-158373 (US2006/017363) may be used. Besides, it is preferable to use the threshold same as previously mentioned first threshold as the fourth threshold.

Figure 29:
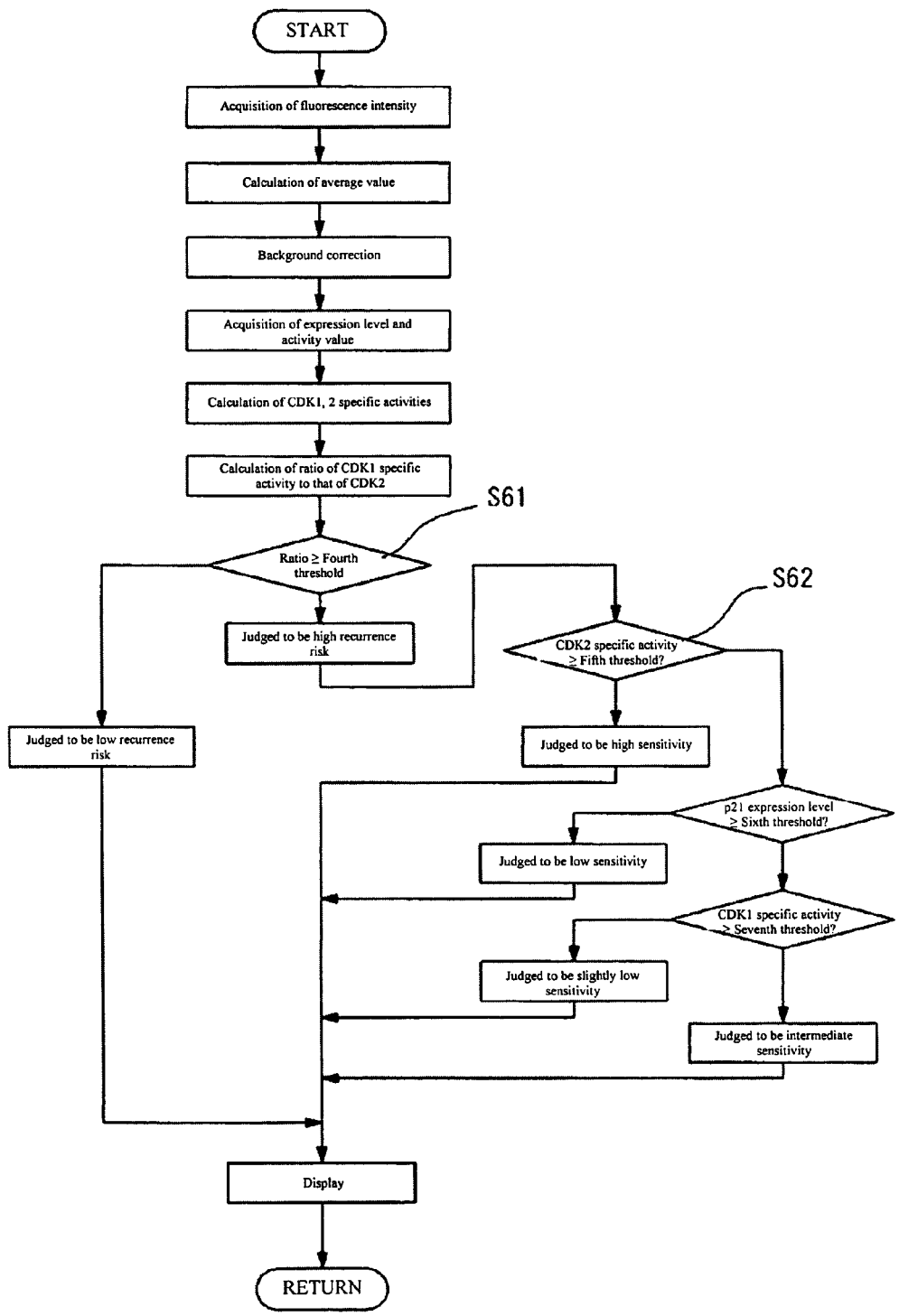
FIG. 29 is a drawing showing entire flow of another example of analytical processing by the determination apparatus.

FIG. 29 is a drawing showing a flowchart of other embodiment of the analytical processing shown in FIG. 28. In this flowchart, a processing to accept selection of the mode is not included in step S1 in FIG. 17, but judgment of recurrence risk is performed in step S61, and sensitivity judgment of anticancer agent is performed for only specimens judged to be higher recurrence risk (step S62). Other steps are same as those shown in FIG. 28.

In the above-shown flowchart, although the determination apparatus A is able to execute judgment of recurrence risk and judgment of sensitivity of anticancer agent, the present invention is not limited thereto, and the present reagent kit may be applied to a determination apparatus which can execute either of judgment.

What is claimed is:

1. A reagent kit for determining a characteristic of tissue obtained from a patient comprising:
   expression measurement reagents for measuring expression level of cyclin-dependant kinase (CDK) in the tissue, the expression measurement reagents comprising:

a first reagent comprising a labeled CDK antibody; and a second reagent comprising a CDK of predetermined concentration;

activity measurement reagents for measuring activity value of CDK in the tissue, the activity measurement reagents comprising:

a third reagent comprising a substrate for the CDK and adenosine 5'-O-(3-thiotriphosphate) (ATP-γS);

a fourth reagent comprising a fluorescent labeling material configured for binding to a reaction product of ATP-γS and the substrate by action of the CDK;

wherein:

a first reagent set of the first and third reagents is stored under a first storage condition relating to temperature;

a second reagent set of the second and fourth reagents is stored under a second storage condition relating to temperature; and the second storage condition is different from the first storage condition.

2. The reagent kit according to claim 1, wherein the first storage condition is cold storage and the second storage condition is frozen storage.

3. The reagent kit according to claim 1, wherein the first reagent set further comprises a fifth reagent for measuring activity value of CDK, the fifth reagent comprising a carrier to which a CDK antibody is immobilized.

4. The reagent kit according to claim 3, wherein the fifth reagent comprises a column containing the carrier.

5. A method for determining a characteristic of tissue obtained from a patient comprising:

measuring expression level of CDK in the tissue by an apparatus, for determining the characteristic of tissue, using the expression measurement reagents of the reagent kit of claim 1, measuring activity value of CDK in the tissue by the apparatus using the activity measurement reagents of the reagent kit of claim 1, and determining the characteristic of the tissue based on the expression level data and the activity value data of CDK obtained by the apparatus.

6. The method according to claim 5, wherein the apparatus comprises:

first data obtaining means for obtaining a first data reflecting expression level of CDK in the tissue, second data obtaining means for obtaining a second data reflecting activity value of CDK in the tissue, and analytical means for obtaining, based on the first data and the second data information relating to the characteristic of the tissue.

7. The reagent kit according to claim 1, wherein the second reagent set further comprises a sixth reagent and a seventh reagent for measuring expression level of CDK, wherein the sixth reagent comprises a protein of predetermined concentration, the protein is coded by a housekeeping gene, and the seventh reagent comprises a labeled antibody against the protein.

8. The reagent kit according to claim 1, wherein the second reagent set further comprises an eighth reagent for measuring expression level and activity value of CDK, the eighth reagent comprising a tissue solubilization solution for preparing a tissue solution by solubilizing the tissue.

9. The reagent kit according to claim 1, wherein the first reagent set comprises a ninth reagent for measuring expression level of CDK, the ninth reagent comprising a protein selected from the group consisting of albumin and casein.

10. The reagent kit according to claim 1, wherein the characteristic of the tissue is selected from the group consisting of proliferation potency of cells contained in the tissue, sensitivity of cells to anticancer agent, malignancy of cancer of the tissue, and combinations thereof.

11. The reagent kit according to claim 1, further comprising a tenth reagent for measuring at least one of the expression level and the activity value of CDK, wherein the tenth reagent is stored under a third storage condition relating to temperature, and the third storage condition is different from the first and the second storage conditions.

12. The reagent kit according to claim 11, wherein the third storage condition is room temperature storage.

* * * * *